US008173408B2

(12) United States Patent
Yusibov et al.

(10) Patent No.: US 8,173,408 B2
(45) Date of Patent: May 8, 2012

(54) RECOMBINANT CARRIER MOLECULE FOR EXPRESSION, DELIVERY AND PURIFICATION OF TARGET POLYPEPTIDES

(75) Inventors: Vidadi Yusibov, Havertown, PA (US); Vadim Mett, Newark, DE (US); Konstantin Musiychuk, Newark, DE (US)

(73) Assignee: Fraunhofer USA, Inc., Plymouth, MI (US)

( * ) Notice: Subject to any disclaimer, the term of this patent is extended or adjusted under 35 U.S.C. 154(b) by 0 days.

(21) Appl. No.: 12/625,129

(22) Filed: Nov. 24, 2009

(65) Prior Publication Data
US 2010/0227373 A1 Sep. 9, 2010

Related U.S. Application Data

(63) Continuation of application No. 10/558,109, filed as application No. PCT/US2004/016452 on May 24, 2004, now abandoned.

(60) Provisional application No. 60/472,495, filed on May 22, 2003.

(51) Int. Cl.
C12P 21/06 (2006.01)
C12N 9/00 (2006.01)
C12N 9/24 (2006.01)
C12N 1/20 (2006.01)
C12N 15/00 (2006.01)
C07H 21/04 (2006.01)

(52) U.S. Cl. .... 435/200; 435/69.1; 435/183; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 4,196,265 A | 4/1980 | Koprowski et al. |
| 4,270,537 A | 6/1981 | Romaine |
| 4,596,556 A | 6/1986 | Morrow et al. |
| 4,653,728 A | 3/1987 | Mochizuki et al. |
| 4,790,824 A | 12/1988 | Morrow et al. |
| 4,816,567 A | 3/1989 | Cabilly et al. |
| 4,886,499 A | 12/1989 | Cirelli et al. |
| 4,935,496 A | 6/1990 | Kudo et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brennerman |
| 5,480,381 A | 1/1996 | Weston |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,693,493 A | 12/1997 | Robinson et al. |
| 5,693,761 A | 12/1997 | Queen et al. |
| 5,693,762 A | 12/1997 | Queen et al. |

(Continued)

FOREIGN PATENT DOCUMENTS

EP 404097 6/1990

(Continued)

OTHER PUBLICATIONS

Chica et al. Curr Opin Biotechnol. Aug. 2005;16(4):378-84.* Sen et al. Appl Biochem Biotechnol. Dec. 2007;143(3):212-23.*
Accession CAA4959, Apr. 18, 2005.
Alignment of 11706573-6 to SEQ ID No. 6 parent matter U.S. Appl. No. 10/558,109, filed Feb. 24, 2009.
Alignment of 11706573-30 to SEQ ID No. 6 parent matter U.S. Appl. No. 10/558,109, filed Feb. 24, 2009.
Alignment of 11706576-12 to SEQ ID No. 6 parent matter U.S. Appl. No. 10/558,109, filed Feb. 24, 2009.
Alignment of 12110877-30 to SEQ ID No. 6 parent matter U.S. Appl. No. 10/558,109, filed Feb. 24, 2009.
Ay et al., "Crystal structures and properties of de novo circularly permuted 1,3-1,4-beta-glucanases," Proteins, 30(2): 155-67, Feb. 1, 1998.
Calandrelli et al., "Purification and characterization of thermostable eylanase and beta-xylosidase by the termophilic bacterium *Bacillus termantarcticus*," Res. Microbiol., 155(4): 283-9, 2004.
Chica et al., "Semi-rational approaches to engineering enzyme activity: combining the benefits of directed evolution and rational design," Current Opinion in Biotechnology, 16:378-384, 2005.

(Continued)

Primary Examiner — Christian Fronda
(74) Attorney, Agent, or Firm — Fish & Richardson P.C.

(57) ABSTRACT

Recombinant carrier molecules having amino acid sequences from thermostable enzymes and methods of use for expression, recovery and delivery of foreign sequences (peptides and polypeptides) produced in different systems (bacteria, yeast, DNA, cell cultures such as mammalian, plant, insect cell cultures, protoplast and whole plants in vitro or in vivo are provided. The recombinant carrier molecule using sequences from lichenase B(Lic B) were also made and used as part of carrier protein to express, recover and deliver a variety of target polypeptides of interest.

20 Claims, 13 Drawing Sheets

U.S. PATENT DOCUMENTS

| | | | |
|---|---|---|---|
| 5,698,417 | A | 12/1997 | Robinson et al. |
| 5,698,426 | A | 12/1997 | Huse et al. |
| 5,702,892 | A | 12/1997 | Mulligan-Kehoe |
| 5,704,911 | A | 1/1998 | Parsons |
| 5,705,154 | A | 1/1998 | Dalie et al. |
| 5,733,743 | A | 3/1998 | Johnson et al. |
| 5,750,078 | A | 5/1998 | Shitara et al. |
| 5,759,817 | A | 6/1998 | Barbas |
| 5,770,403 | A | 6/1998 | Dalie et al. |
| 5,770,429 | A | 6/1998 | Lonberg et al. |
| 5,855,866 | A | 1/1999 | Thorpe et al. |
| 5,877,289 | A | 3/1999 | Thorpe et al. |
| 5,888,789 | A | 3/1999 | Rodriguez et al. |
| 5,893,397 | A | 4/1999 | Peterson et al. |
| 5,965,132 | A | 10/1999 | Thorpe et al. |
| 5,993,412 | A | 11/1999 | Deily et al. |
| 6,004,555 | A | 12/1999 | Thorpe et al. |
| 6,042,832 | A | 3/2000 | Koprowski et al. |
| 6,093,399 | A | 7/2000 | Thorpe et al. |
| 6,103,511 | A | 8/2000 | Li et al. |
| 6,261,535 | B1 | 7/2001 | Thorpe et al. |
| 6,524,825 | B1 | 2/2003 | Mizzen et al. |
| 6,649,172 | B2 | 11/2003 | Johnson |
| 6,740,740 | B2 | 5/2004 | Garger et al. |
| 6,797,491 | B2 | 9/2004 | Neefe, Jr. et al. |
| 6,841,659 | B2 | 1/2005 | Turpen et al. |
| 7,888,135 | B2 | 2/2011 | Tarleton et al. |
| 2004/0093643 | A1 | 5/2004 | Ensley |
| 2004/0170606 | A1 | 9/2004 | Palmer et al. |
| 2004/0268442 | A1 | 12/2004 | Miller et al. |
| 2005/0026291 | A1 | 2/2005 | Fedorkin et al. |
| 2005/0042229 | A1 | 2/2005 | Yang et al. |
| 2005/0048074 | A1 | 3/2005 | Cardineau et al. |
| 2005/0186621 | A1 | 8/2005 | Galarza et al. |
| 2006/0008473 | A1 | 1/2006 | Yang et al. |
| 2006/0265787 | A1 | 11/2006 | Piruzian et al. |
| 2007/0275014 | A1 | 11/2007 | Yusibov et al. |
| 2008/0124272 | A1 | 5/2008 | Yusibov et al. |
| 2008/0279877 | A1 | 11/2008 | Yusibov et al. |
| 2009/0324634 | A1 | 12/2009 | Knapp et al. |
| 2011/0027304 | A1 | 2/2011 | Yusibov et al. |
| 2011/0059130 | A1 | 3/2011 | Yusibov |

FOREIGN PATENT DOCUMENTS

| | | |
|---|---|---|
| WO | WO9311161 | 6/1993 |
| WO | WO9602555 | 2/1996 |
| WO | WO9612028 | 4/1996 |
| WO | WO9713537 | 4/1997 |
| WO | WO9737705 | 10/1997 |
| WO | WO98/14595 | 4/1998 |
| WO | WO9845331 | 10/1998 |
| WO | WO9907860 | 2/1999 |
| WO | WO0020612 | 4/2000 |
| WO | WO0025574 | 5/2000 |
| WO | WO0046350 | 8/2000 |
| WO | WO03040179 | 5/2003 |
| WO | WO2004043886 | 5/2004 |
| WO | WO2005026375 | 3/2005 |
| WO | WO2005049839 | 6/2005 |
| WO | WO2005067620 | 7/2005 |
| WO | WO2005081905 | 9/2005 |
| WO | WO2006003018 | 1/2006 |
| WO | WO2006124712 | 11/2006 |
| WO | WO2007089753 | 8/2007 |
| WO | WO2007095304 | 8/2007 |
| WO | WO2007095318 | 8/2007 |
| WO | WO2007149715 | 12/2007 |
| WO | WO2008021959 | 2/2008 |
| WO | WO2008033105 | 3/2008 |
| WO | WO2008033159 | 3/2008 |
| WO | WO2008048945 | 4/2008 |
| WO | WO2008110937 | 9/2008 |
| WO | WO2008134643 | 11/2008 |
| WO | WO2009009759 | 1/2009 |
| WO | WO2009026397 | 2/2009 |
| WO | WO2009054708 | 4/2009 |
| WO | WO2009058355 | 5/2009 |
| WO | WO2010036970 | 4/2010 |
| WO | WO2010037046 | 4/2010 |

OTHER PUBLICATIONS

Hahn et al., "Native like in vivo folding of a circularly permuted jellyroll protein shown by crystal structure analysis," Proc Natl Acad Sci USA, 91(22): 10417-21, Oct. 25, 1994.

Johnson et al., Respratory syncytial virus (RSV) G glycoprotein is not necessary for vaccine-enhanced disease induced by immunization with formalin-inactivated RSV, J. Virol, 78(11):6024-32, 2004.

Moreira et al., "A Thermostable Maltose-tolerant α-anylase from *Asperillgus tamarii*," J. Basic Microbiology, 44: 29-35, 2004.

Moayeri et al., "The roles of anthrax toxin in pathogenesis," Curr Opin Microbiol, 7(1):19-24, 2004.

Musiychuk et al., Preparation and properties of *Clostribdium termocellum* lichenase deletion variants and their use for construction of bifunctional hybrid proteins, Biochemistry Mosc., (65(12): 1397-402, Dec. 2000.

Piruzian et al., "A reporter system for prokaryotic and eukaryotic cells based on the thermostable lichenase from *Clostridium thermocellum*," Mol Genet Genomics, 266(5): 778-86, Jan. 2002, Epub Nov. 27, 2001.

Piruzian et al., "The use of a thermostable B-glucanase gene from *Clostridium thermocellum* as a reporter gene in plants," Mol Gen Genet 257(50): 561-7, Mar. 1998.

Sen et al., Appl Biochem Biotechnol., 143(3):212-23, Dec. 2007.

Shima et al., "hyperthermaphilic and salt-dependent formytransferase from *Methanopyrus kanleri*," Biochem Soc. Trans., 32:269-72, 2004.

Stewart et al., "Mutant barley ($1\rightarrow3,1\rightarrow4$)-β-glucan endohydrolases with enhanced thermostability", Protein Engineering, vol. 14, No. 4, pp. 245-253, (2001).

Tsai et al., "Crystal structure of a natural circularly permuted jellyroll protein: 1,3-1,4-beta-D-glucanase from *Fibrobacter succinogens*," J Mol Biol., 330(3):607-20, Jul. 11, 2003.

Wang et al., "Structural Basis for Thermostability of β-Glycosidase from the Thermophilic Eubacterium *Thermus nonproteolyticus* HG102," J. Bacteriology, 185: 4248-55, 2003.

Wiesmuller et al., "Peptid Vaccines and Peptide Libraries," Biol Chem., 382(4): 571-9, Apr. 2001.

Communication corresponding to European Appln. No. 04 776 107.7 date Sep. 23, 2009.

International Search Report, PCT/US04/16452, date of mailing Dec. 23, 2005.

Communication dated Sep. 23, 2009 for European Appln. No. 04 776 107.7 (3 pgs.).

Communication dated Apr. 21, 2010 for European Appln. No. 04 776 107.7 (4 pgs.).

Communication dated May 20, 2010 for European Appln. No. 04 776 107.7 (3 pgs.).

Supplementary European Search Report dated Dec. 5, 2006 for European Appln. No. EP 04 77 6107 (2 pgs.).

Ahlquist et al., "Gene Expression Vectors Derived from Plant RNA Viruses," *Current Communications in Molecular Biology—Viral Vectors*, 183-189, 1988.

Air, "Mechanism of antigenic variation in an individual epitope on influenza virus N9 neuraminidase," J. Virology, 64(12):5797-5803, 1990.

Akol and Murray, "*Trypanosoma congolense*: Susceptibility of cattle to cyclical challenge," Exp. Parasitol., 55:386-393, 1983.

Alvarez et al., "Plant-made subunit vaccine against pneumonic and bubonic plague is orally immunogenic in mice," Vaccine, 24(14):2477-2490, 2006.

Anderson et al., "Recombinant V Antigen Protects Mice against Pneumonic and Bubonic Plague Caused by F1-Capsule-Positive and -Negative Strains of *Yersinia pestis*," Infect. Immun., 64(11):4580-5, 1996.

Andrews et al., "Fraction 1 Capsular Antigen (F1) Purification from *Yersinia pestis* CO92 and from an *Escherichia coli* Recombinant Strain and Efficacy against Lethal Plague Challenge," *Infect. Immun*., 64(6):2180-7, 1996.

Aymard et al., "Role of antineuraminidase antibodies in protection against influenza," *Bulletin de l'Academie nationale de medicine*, 182(8): 1723-1736 (1998).

Aymard et al., "Neuraminidase assays," *Developments in Biologicals*, 115:75-83 (2003).

Barbas et al., "Assembly of combinatorial antibody libraries on phage surfaces: The gene III site," *Proc. Natl. Acad. Sci. USA*, 88:7978, 1991.

Barbas et al., "Semisynthetic combinatorial antibody libraries: A chemical solution to the diversity problem," *Proc. Natl. Acad. Sci. USA*, 89:4457, 1992.

Barfield et al., "Gene Transfer in Plants of *Brassica juncea* Using *Agrobacterium tumefaciens*-Mediated Transformation," *Plant Cell Reports*, 10(6/7):308-14, 1991.

Bates, "Genetic Transformation of Plants by Protoplast Electroporation," *Molecular Biotechnol.*, 2(2):135-145, 1994.

Beachy et al., "A Genetic Map for the Cowpea Strain of TMV," *Virology*, 73:498-507, 1976.

Bedell et al., "The E6-E7 Region of Human Papillomavirus Type 18 is Sufficient for Transformation of NIH 3T3 and Rat-1 Cells," *J. Virol.*, 61:3635-40, 1987.

Berger et al., "Therapeutic applications of monoclonal antibodies," *Am J Med Sci.*, 324(1):14-30, 2002.

Bisaro et al., "Genetic Analysis of Tomato Golden Mosaic Virus," *Current Communications in Molecular Biology: Viral Vectors*, 172-189, 1988.

Brett et al., "Immunization against influenza A virus: comparison of conventional inactivated, live-attenuated and recombinant baculovirus produced purified hemagglutinin and neuraminidase vaccines in a murine model system," *Virology*, 339(2):273-280, 2005.

Broothaerts et al., "Gene Transfer to Plants by Diverse Species of Bacteria," *Nature*, 433:629-633, 2005.

Brodzik et al., "Advances in alfalfa mosaic virus-mediated expression of anthrax antigen in planta," *Biochem. Biophys. Res. Commun.*, 338(2):717-722, 2005.

Bol et al., "A Functional Equivalence of Top Component a RNA and Coat Protein in the Initiation of Infection by Alfalfa Mosaic Virus," *Virology*, 46:73-85, 1971.
Bol et al., "Alfalfa Mosaic Virus and Ilarviruses: Involvement of Coat Protein in Multiple Steps of the Replication Cycle," *J. Gen. Virol.*, 80:1089-1102, 1999.
Boyd and Beeson., "Animal models for evaluation of compounds against influenza viruses," *Journal of Antimicrobial Chemotherapy*, 1:43-47, 1975.
Bruening et al., "In Vitro and in Vivo Translation of the Ribonucleic Acids of a Cowpea Strain of Tobacco Mosaic Virus," *Virology*, 71:498-517, 1976.
Burke et al., "Cloning of Large Segments of Exogenous DNA into Yeast by Means of Artificial Chromosome Vectors," *Science*, 236:806, 1987.
Buscaglia et al., "Tandem amino acid repeats from *Trypanosoma cruzi* shed antigens increase the half-life of proteins in blood," *Blood*, 93(6):2025-2032, 1999.
Canizares et al., "Use of viral vectors for vaccine production in plants," *Immunol. Cell Biol.*, 83:263-270, 2005.
Chain et al., "Complete Genome Sequence of *Yersinia pestis* Strains Antigua and Nepal516: Evidence of Gene Reduction in an Emerging Pathogen," *J. Bacteriol.*, 188(12):4453-63, 2006.
Chen et al., "Complete sequence of the binary vector pB1121 and its application in cloning T-DNA insertion from transgenic plants," *Mol. Breed.*, 11:287-293, 2003.
Chen et al., "Induction and relief of nasal congestion in ferrets infected with influenza virus," *Int. J. Exp. Path.*, 76:55-64, 1995.
Chichester et al., "Different response requirements for IFN-γ production in ELISPOT assays by CD4+ T cells from mice early and late after submission," *J. Immunol. Methods*, 309:99-107, 2006.
Chichester et al., "Immunogenicity of a subunit vaccine against *Bacillus anthracis," Vaccine*, 25:3111-3114, 2007.
Corbel, "Reasons for instability of bacterial vaccines," *Developments in Biological Standardization*, 87:113-124, 1996.
Costa et al., "Conformational stability and antibody response to the 18kDa heat-shock protein formulated into different vehicles," *Applied Biochemistry and Biotechnology*, 73(1):19-28, 1998.
Crossway et al., "Integration of foreign DNA following microinjection of tobacco mesophyll protoplasts," *Mol. Gen. Genet.*, 202:179-185, 1986.
Curtis and Nam, "Transgenic radish (*Raphanus sativus* L. *longipinnatus* Bailey) by floral-dip method—plant development and surfactant are important in optimizing transformation efficiency," *Transgenic Research*, 10(4):363-371, 2001.
Dawson et al., "cDNA cloning of the complete genome of tobacco mosaic virus and production of infectious transcripts," *Proc. Natl Acad. Sci.*, USA, 83:1832, 1986.
DeGraff et al., "In Vitro Evidence that the Coat Protein of Alfalfa Mosaic Virus Plays a Direct Role in the Regulation of Plus and Minus RNA Synthesis Implications for the Life Cycle of Alfalfa Mosaic Virus," *Virology*, 208:583-589, 1995.
Deng et al., "Genome Sequence of *Yersinia pestis* KIM," *J. Bacteriol.*, 184(16):4601-11, 2002.
Desfeux et al., "Female Reproductive Tissues Are the Primary Target of *Agrobacterium*-Mediated Transformation by the Arabidopsis Floral-Dip Method," *Plant Physiology*, 123(3):895-904, 2000.
Dréau et al., "Human Papilloma Virus in Melanoma Biopsy Specimens and Its Relation to Melanoma Progression," *Annals of Surgery*, 231:664-671, 2000.
Fenton et al., "Immunity to Influenza in Ferrets. XIV: Comparative Immunity Following Infection or Immunization with Live or Inactivated Vaccine," *Br. J. Exp. Path.*, 62:297, 1981.
Fernando et al., "Expression, purification and immunological characterization of the transforming protein E7, from cervical cancer-associated human papillomavirus type 16," *Clin Exp Immunol*, 115:397-403, 1999.
Flick-Smith et al., "A Recombinant Carboxy-Terminal Domain of the Protective Antigen of *Bacillus anthracis* Protects Mice against Anthrax Infection," *Infect. Immun.*, 70:1653-1656, 2002.
Floss et al., "Production of vaccines and therapeutic antibodies for veterinary applications in transgenic plants: an overview," *Transgenic Research*, 16(3):315-332, 2007.
Fraley et al., "Liposome-Mediated Delivery of Tobacco Mosaic Virus RNA into Tobacco Protoplasts: A Sensitive Assay for Monitoring Liposome-Protoplast Interactions," *Proc. Natl. Acad. Sci. USA*, 79:1859-1863, 1982.
Fraley et al., "Expression of Bacterial Genes in Plant Cells," *Proc. Natl. Acad. Sci. USA*, 80:4803-4807, 1983.
Franconi et al., "Plant-derived Human Papillomavirus 16 E7 Oncoprotein Induces Immune Response and Specific Tumor Production," *Cancer Res.*, 62:3654, 2002.
Fromm et al., "Expression of Genes Transferred into Monocot and Dicot Plant Cells by Electroporation," *Proc. Natl. Acad. Sci. USA*, 82:5824, 1985.
Fütterer et al., "Use of DNA Plant Viruses and Plant Viral Expression Signals for Gene Expression in Plants and Plant Protoplasts," *Current Communications in Molecular Biology—Viral Vectors*, 178-182, 1988.
Gelvin, "Agrobacterium-Mediated Plant Transformation: the Biology behind the 'Gene-Jockeying' Tool," *Microbiol. Mol Biol. Rev.*, 67(1):16-37, 2003.
Giri and Narasu, "Transgenic hairy roots: recent trends and applications," *Biotechnol. Adv.*, 18:1-22, 2000.
Gleba et al., "Magnifection—a new platform for expressing recombinant vaccines in plants," *Vaccine*, 23:2042-2048, 2005.
Goldenkova et al., "A Thermostable *Clostridium thermocellum* Lichenase-based Reporter System for Studying the Gene Expression Regulation in Prokaryotic and Eukaryotic Cells," *Mol. Biol.*, 36:698-704, 2002.
Green et al., "Transient protein expression in three *Pisum sativum* (green pea) varieties," *Biotechnology Journal*, 4(2):230-237, 2009.
Grierson et al., "Plant Viruses," *Plant Molecular Biology*, 126-146, 1984.
Gu et al., "Protection against anthrax toxin by vaccination with a DNA plasmid encoding anthrax protective antigen," *Vaccine*, 17:340, 1999.
Heath et al., "Protection against experimental bubonic and pneumonic plague by a recombinant capsular F1-V antigen fusion protein vaccine," *Vaccine*, 16(11/12):1131-7, 1998.

Hellens et al., "pGreen: a versatile and flexible binary Ti vector for *Agrobacterium*-mediated plant transformation," *Plant Molecular Biology*, 42: 819-832, 2000.

Herbert and Lumsden, "*Trypanosoma brucei*: a rapid 'matching' method for estimating the host's parasitemia," *Exp. Parasitol*, 40:427, 1976.

Hobson et al., "The role of serum haemagglutination-inhibiting antibody in protection against challenge infection with influenza A2 and B viruses," *J. Hyg.*, 70:767, 1972.

Huang et al., "Plant-derived measles virus hemagglutinin protein induces neutralizing antibodies in mice," *Vaccine*, 19(15-16):2163-2171, 2001.

Huber et al., "Distinct Contributions of Vaccine-Induced Immunoglobulin G1 (IgG1) and IgG2a Antibodies to Protective Immunity against Influenza," *Clin. Vaccine Immunol.*, 13:981-90, 2006.

Hull et al., "Human-derived, plant-produced monoclonal antibody for the treatment of anthrax," *Vaccine*, 23:2082-2086, 2005.

Hunter et al., "Messenger RNA for the Coat Protein of Tobacco Mosaic Virus," *Nature*, 260:759-760, 1976.

Huse et al., "Generation of a Large Combinatorial Library of the Immunoglobulin Repertoire in Phage Lambda," *Science*, 246:1275, 1989.

Ishikawa et al., "In Vitro Mutagenesis of the Putative Replicase Genes of Tobacco Mosaic Virus," *Nucleic Acids Res*. 14:8291-8308, 1986.

Jaspars et al., "Plant Viruses with a Multipartite Genome," *Adv. Virus Res*. 19:37-149, 1974.

Jirholt et al., "Exploiting sequence space: shuffling in vivo formed complementarity determining regions into a master framework," *Gene*, 215:471, 1998.

Jones et al., "Replacing the complementarity—determining regions in a human antibody with those from a mouse," *Nature*, 321:522, 1986.

Kang et al., "Linkage of recognition and replication functions by assembling combinatorial antibody Fab libraries along phage surfaces," *Proc. Natl. Acad. Sci USA*, 88:4363, 1991.

Kao et al., "A Method for High-frequency Intergeneric Fusion of Plant Protoplasts," *Planta*, 115:355, 1974.

Kapila et al., "An Agrobacterium-mediated transient gene expression system for intact leaves," *Plant Sci.*, 122:101-108, 1997.

Kapusta et al., "A plant-derived edible vaccine against hepatitis B virus," *FASEB J.*, 13:1796-1799, 1999.

Katayama and Mine, "*Quillaja* Saponin Can Modulate Ovalbumin-Induced IgE Allergic Responses through Regulation of Th1/Th2 Balance in a Murine Model," *J. Agric. Food Chem.*, 54:3271-6, 2006.

Kikkert et al., "Biological Projectiles (Phage, Yeast, Bacteria) for Genetic Transformation of Plants," *In Vitro Cell. Dev. Bio.—Plant*, 35(1):43-50, 1999.

Klein et al., "High-velocity microprojectiles for delivering nucleic acids into living cells," *Nature*, 1987, 327:70-73.

Knapp et al., "Conundrum of the Lack of Defective RNAs (dRNAs) Associated with Tobamovirus Infections: dRNAs That Can Move Are Not Replicated by the Wild-Type Virus; dRNAs That Are Replicated by the Wild-Type Virus Do Not Move," *J. Virol.*, 75:5518, 2001.

Knudsen and Muller, "Transformation of the developing barley endosperm by particle bombardment," *Planta*, 185:330-336, 1991.

Konieczny et al., "The Combination of IgM Subunits and Proteolytic IgG Fragments by Controlled Formation of Interchain Disulphides," *Haematologia (Budap.)*, 14:95, 1981.

Krens et al., "In vitro transformation of plant protoplasts with Ti-plasmid DNA," *Nature*, 296:72-74, 1982.

Kubler-Kielb et al., "Long-lasting and transmission-blocking activity of antibodies to *Plasmodium falciparum* elicited in mice by protein conjugates of Pfs25," *Proceedings of the National Academy of Sciences of USA*, 104(1):293-298, 2007.

Kumagai et al., "Rapid, High-Level Expression of Glycosylated Rice α-Amylase in Transfected Plants by an RNA Viral Vector," *Gene*, 245:169-174, 2000.

Lambkin et al., "Strong local and systemic protective immunity induced in the ferret model by an intranasal virosome-formulated influenza subunit vaccine," *Vaccine*, 22:4390, 2004.

Lawton et al., "Expression of a Soybean (3-Conclycinin Gene Under the Control of the Cauliflower Mosaic Virus 35S and 19S Promoters in Transformed Petunia Tissues," *Plant Mol. Biol*, 9:315-324, 1987.

Lee and Air, "Contacts between influenza virus N9 neuraminidase and monoclonal antibody NC10," *Virology*, 300(2):255-268, 2002.

Leite et al., "Expression of correctly processed human growth hormone in seeds of transgenic tobacco plants," *Molecular Breeding*, 6:47-53, 2000.

Lensen et al., "Measurement by membrane feeding of reduction in *Plasmodium falciparum* transmission induced by endemic sera," *Trans R Soc Trop Med Hyg.*, 90(1):20-2, 1996.

Lewandowski and Dawson, "Deletion of Internal Sequences Results in Tobacco Mosaic Virus Defective RNAs That Accumulate to High Levels without Interfering with Replication of the Helper Virus," *Virology*, 251:427-437, 1998.

Li et al., "Immunization with recombinant beta-tubulin from *Trypanosoma evansi* induced protection against *T. evansi*, *T. equiperdum* and *T. b. brucei* infection in mice," *Parasite Immunology*, 29:191-199, 2007.

Lim et al., "An Anthrax Lethal Factor-Neutralizing Monoclonal Antibody Protects Rats before and after Challenge with Anthrax Toxin," *Infection and Immunity*, 73:6547, 2005.

Lin et al., "Treatment of Established Tumors with a Novel Vaccine That Enhances Major Histocompatibility Class II Presentation of Tumor Antigen," *Cancer Research*, 56:21, 1996.

Little et al., "Passive Protection by Polyclonal Antibodies against *Bacillus anthracis* Infection in Guinea Pigs," *Infect. Immun.*, 65:5171-5175, 1997.

Loesch-Fries et al., "Expression of Alfalfa Mosaic Virus RNA 4 cDNA Transcripts in Vitro and in Vivo," *Virology*, 146:177-187, 1985.

Lorence and Verpoorte, "Gene transfer and expression in plants," *Methods Mol. Biol.*, 267:329-350, 2004.

Lubega et al., "Immunization with a tubulin-rich preparation from *Trypanosoma brucei* confers broad protection against African trypanosomosis," *Exp. Parasitol.*, 102:9-22, 2002.

Lubega et al., "*Trypanosoma brucei*: anti-tubulin antibodies specifically inhibit trypanosome growth in culture," *Exp. Parasitol.*, 102:134-142, 2002.

Maassab et al., "Evaluation of a Cold-Recombinant Influenza Virus Vaccine in Ferrets," *The Journal of Infectious Diseases*, 146(6):780-790, 1982.

Maliga et al., "Transient Cycloheximide Resistance in a Tobacco Cell Line," *Mol. Gen. Genet.*, 149:267-271, 1976.

Mathew, Plant Viruses Online—Cassava Indian mosaic bigeminvirus (http://imagels.uidaho.eduivide/), downloaded on Feb. 21, 2006, 5 pgs.

Mbawuike et al., "Humoral and cell-mediated immune responses of humans to inactivated influenza vaccine with or without QS21 adjuvant," *Vaccine*, 25:3263-9, 2007.

McCormick et al., "Rapid Production of Specific Vaccines for Lymphoma by Expression of the Tumor-Derived Single-Chain Fv Epitopes in Tobacco Plants," *Proc. Natl. Acad. Sci. USA*, 96:703-708, 1999.

McHugh et al., "Improved stability of a protein vaccine through elimination of a partially unfolded state," *Protein Science*, 13:2736-2743, 2004.

Mellin et al., "Human Papillomavirus (HPV) DNA in Tonsillar Cancer: Clinical Correlates, Rise of Relapse, and Survival," *International Journal of Cancer*, 89:300-304, 2000.

Menczel et al. "Streptomycin Resistant and Sensitive Somatic Hybrids of *Nicotiana tabacum* + *Nicotiana knightiana*: Correlation of Resistance to *N. tabacum* Plastids," *Theor. Appl. Genet.*, 59, 191-195, 1981.

Meshi et al., "Function of the 30 kd Protein of Tobacco Mosaic Virus: Involvement in Cell-to-Cell Movement and Dispensability for Replication," *EMBO J.*, 6:2557-63, 1987.

Mett et al., "Plants as biofactories," *Biologicals: Journal of the International Association of Biological Standardization*, 36(6):354-358, 2008.

Mett et al., "A plant-produced plague vaccine candidate confers protection to monkeys," *Vaccine*, 25(16):3014-3017, 2007.

Mett et al., "A plant-produced influenza subunit vaccine protects ferrets against virus challenge," *Influenza and Other Respiratory Viruses*, 2(1):33-40, 2008.

Modelska et al., "Immunization against rabies with plant-derived antigen," *Proc. Natl. Acad. Sci.*, USA, 95:2481-2485, 1998.

Morrison et al., "Chimeric human antibody molecules: Mouse antigen-binding domains with human constant region domains," *Proc. Natl. Acad. Sci USA*, 81:6851, 1984.

Morrison et al., "Production of Novel Immunoglobulin Molecules by Gene Transfection," *Mt. Sinai J. Med.*, 53:175, 1986.

Murashige et al., "A Revised Medium for Rapid Growth and Bio Assays with Tobacco Tissue Cultures," *Physiologia Plantarum*, 15:473, 1962.

Musiychuk et al., "A launch vector for the production of vaccine antigens in plants," *Influenza and Other Respiratory Viruses*, 1:1, 2007.

Nagy et al., "Thermal stability of chemically denatured green fluorescent protein (GFP)—A preliminary study," *Thermochimica Acta*, 410(1), abstract, 2004.

Nass, "Anthrax Vaccine—Model of a Response to the Biologic Warfare Threat," *Infect. Dis. Clin. North Am.*, 13,187-208, 1999.

NCBI GenBank Accession No. ABP96852, "Influenza A virus" (A/Egypt/2616-NAMRU3/2007(H5N1)) hemagglutinin (HA) gene, complete CDS, 30, Apr. 2007.

NCBI GenBank Accession No. AAS93885, "Influenza A virus" (A/Cheju/274/2002(H3N2)) neuraminidase (NA) gene, complete CDS, 25, Apr. 2004.

Neeleman et al., "Role of Alfalfa Mosaic Virus Coat Protein Gene in Symptom Formation" *Virology*, 181: 687-693, 1991.

Neeleman et al., "Infection of Tobacco with Alfalfa Mosaic Virus cDNAs Sheds Light on the Early Function of the Coat Protein," *Virology*, 196:883-887, 1993.

Park et al., "Molecular Biology of Cervical Cancer and Its Precursors," *Cancer*, 76:1902-1913, 1995.

Parkhill et al., "Genome sequence of *Yersinia pestis*, the causative agent of plague," *Nature*, 413:523-7, 2001.

Peres et al., "Shoot regeneration capacity from roots and transgenic hairy roots of tomato cultivars and wild related species," *Plant Cell, Tissue, and Organ Culture*, 65:37-44, 2001.

Petosa et al., "Crystal structure of the anthrax toxin protective antigen," *Nature*, 385:833-838, 1997.

Pilon-Smits et al., "Overexpression of ATP Sulfurylase in Indian Mustard Leads to Increased Selenate Uptake, Reduction, and Tolerance," *Plant Physiol.*, 119(1): 123-132, 1999.

Potter et al., "Immunity to Influenza in Ferrets II. Influence of Adjuvants on Immunization," *Br. J. Exp. Pathol.*, 53:168, 1972.

Potter et al., "Immunity to Influenza in Ferrets VI. Immunization with Adjuvanted Vaccines," *Arch. Gesamte Virusforsch.*, 42:285, 1973.

Potter et al., "Immunity to influenza in ferrets V. Immunization with inactivated virus in adjuvant 65," *J. Hyq. Lond.*, 71:97, 1973.

Pruett et al., "Critical interactions in binding antibody NC41 to influenza N9 neuraminidase: amino acid contacts on the antibody heavy chain," *Biochemistry*, 37:10660-10670, 1998.

Qian et al., "Conjugating recombinant proteins to *Pseudomonas aeruginosa* ExoProtein A: A strategy for enhancing immunogenicity of malaria vaccine candidate," *Vaccine*, 25(20): 3923-3933, 2007.

Qing et al., "Transformation of Pakchoi (*Brassica rapa* L. ssp. *chinensis*) by *Agrobacterium* Infiltration," *Molecular Breeding*, 1:67-72, 2000.

Rao and Ravishankar, "Plant cell cultures: Chemical factories of secondary metabolites," *Biotechnol. Adv.*, 20:101-153, 2002.

Rasooly-Balaban, "Trypanosome microtubule-associated protein p15 as a vaccine for the prevention of African sleeping sickness," *Vaccine*, 22(8):1007-1015, 2004.

Reinstein et al., Degradation of the E7 human papillomavirus oncoprotein by the ubiquitin-proteasome system: targeting via ubiquitination of the N-terminal residue, *Oncogene*, 19:5944-5950, 2000.

Riechmann et al., "Reshaping human antibodies for therapy," *Nature*, 332:323, 1988.

Riva et al., "*Agrobacterium tumefaciens*: a natural tool for plant transformation," *EJB Electronic J. Biotech.*, 1(3), 118-133, 1998.

Rowe et al., "Detection of Antibody to Avian Influenza A (H5N1) Virus in Human Serum by Using a Combination of Serologic Assays," *J. Clin. Microbiol.*, 37:937-43, 1999.

Sabbatini et al., "Pilot Study of a Heptavalent Vaccine-Keyhole Limpet Hemocyanin Conjugate plus QS21in Patients with Epithelial Ovarian, Fallopian Tube, or Peritoneal Cancer," *Clin. Cancer Res.*, 13:4170-7, 2007.

Saito et al., "Long-Distance Movement and Viral Assembly of Tobacco Mosaic Virus Mutants," *Virology*, 176:329-336, 1990.

Santi et al., "Protection conferred by recombinant *Yersinia pestis* antigens produced by a rapid and highly scalable plant expression system," *Proc. Natl. Acad. Sci. USA*, 103(4): 861-866, 2006.

Saravolac et al "Immunoprophylactic strategies against respiratory influenza virus infection," *Vaccine*, 19(17-19):2227-32, 2001.

Scheiblauer et al., "Pathogenicity of influenza A/Seal/Mass/1/80 virus mutants for mammalian species," *Arch Virol*, 140:341-384, 1995.

Schell et al., "Transgenic Plants as Tools to Study the Molecular Organization of Plant Genes," *Science*, 237:1176-1183, 1987.

Schild et al., "A single-radial-immunodiffusion technique for the assay of influenza haemagglutinin antigen—Proposals for an assay method for the haemagglutinin content of influenza vaccines," *Bull. World Health Org.*, 52:223-31, 1975.

Seedorf et al., "Human Papillomavirus Type 16 DNA Sequence," *Virology*, 145:181, 1985.

Shimasaki et al., "Rapid diagnostics: the detection of neuraminidase activity as a technology for high-specificity targets," *Philosophical transactions of the Royal Society of London. Series B, Biological Sciences*, 356(1416):1925-1931, 2001.

Shivprasad et al., "Heterologous Sequences Greatly Affect Foreign Gene Expression in Tobacco Mosaic Virus-Based Vectors," *Virology*, 255(2):312-23, 1999.

Shoji et al , "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 27(25-26):3467-3470, 2009.

Shoji et al., "Plant-expressed HA as a seasonal influenza vaccine candidate," *Vaccine*, 26(23):2930-2934, 2008.

Singh et al., "Gln277 and Phe544 residues are involved in thermal inactivation of protective antigen of *Bacillus anthracis*," *Biochemical and Biophysical Research Communications*, 296:1058-1062, 2002.

Singh et al., "Study of Immunization against Anthrax with the Purified Recombinant Protective Antigen of *Bacillus anthracis*," *Infect. Immun.*, 66:3447-3448, 1998.

Singh et al., "Thermal inactivation of protective antigen of *Bacillus anthracis* and its prevention by polyol osmolytes," *Biochemical and Biophysical Research Communications*, 322:1029-1037, 2004.

Smahel et al., "Modified HPV16 E7 Genes as DNA Vaccine against E7-Containing Oncogenic Cells," *Virology*, 281:231-238, 2001.

Snow et al., "The global distribution of clinical episodes of *Plasmodium falciparum* malaria," *Nature*, 434:214-217, 2005.

Soderlind et al., "Commentary—Complementarity-determining region (CDR) implantation: a theme of recombination," *Immunotechnol.*, 4:279, 1999.

Soderlind et al., "Recombining germline-derived CDR sequences for creating diverse singleframework antibody libraries," *Nature Biotechnol.*, 18:852, 2000.

Soini et al., "Presence of human papillomavirus DNA and abnormal p53 protein accumulation in lung carcinoma," *Thorax*, 51:887-893, 1996.

Spilliaert et al., "Cloning and sequencing of a *Rhodothermus marinus* gene, *bglA*, coding for a thermostable beta-glucanase and its expression in *Escherichia coli*," *Eur. J. Biochem.*, 224(3):923-930, 1994.

Tacket et al., "Human Immune Responses to a Novel Norwalk Virus Vaccine Delivered in Transgenic Potatoes," *J. Infect. Dis.*, 182:302-305, 2000.

Thanavala et al., "Immunogenicity in humans of an edible vaccine for hepatitis B," *Proc. Natl. Acad. Sci.*, USA, 102:3378-3382, 2005.

Thomas et al., "HPV-18 E6 mediated inhibition of p53 DNA binding activity is independent of E6 induced degradation," *Oncogene*, 10:261-8, 1995.

Throsby et al., "Heterosubtypic neutralizing monoclonal antibodies cross-protective against H5NI and H1N1 recovered from human IgM+ memory B cells," *Plos One, LNKD-PUBMED*:19079604, 3(12):E3942, 2008.
Toms et al., "Behaviour in Ferrets of Swine Influenza Virus Isolated from Man," *The Lancet*, 68-71, 1977.
Turpen et al., "Transfection of whole plants from wounds inoculated with *Agrobacterium tumefaciens* containing cDNA of tobacco mosaic virus," *J. Virol, Methods*, 42:227, 1993.
UniProt Database [Online] EBI Accession No. Q0PDN1, "SubName: Full=Hemagglutinin," Sep. 5, 2006.
UniProt Database [Online] EBI Accession No. A9X0E7, "SubName: Full=Hemagglutinin; Flags: Precursor," Feb. 5, 2008.
UniProt Database accession No. P04107 Nov. 1, 1986.
Van der Kolk et al., "Evaluation of the standard membrane feeding assay (SMFA) for the determination of malaria transmission-reducing activity using empirical data," *Parasitology*, 130(Pt 1):13-22, 2005 (with Erratum in: Parasitology 131(Pt 4):578, 2005).
Van Der Kuyl et al., "Complementation and Recombination between Alfalfa Mosaic Virus RNA3 Mutants in Tobacco Plants," *Virology*, 183:731-738, 1991.
Van Der Kuyl et al., "Role of Alfalfa Mosaic Virus Coat Protein in Regulation of the Balance between Viral Plus and Minus Strand RNA Synthesis," *Virology*, 185:496-499, 1991.
Van Der Vossen et al., "Early and Late Functions of Alfalfa Mosaic Virus Coat Protein Can Be Mutated Separately," *Virology*, 202:891-903, 1994.
Verch et al., "Expression and assembly of a full-length monoclonal antibody in plants using a plant virus vector," *J. Immunol. Methods*, 220, 69-75, 1998.
Voinnet et al., "An enhanced transient expression system in plants based on suppression of gene silencing by the p19 protein of tomato bushy stunt virus," *Plant J.*, 33:949, 2003.
Volten-Doting, Plant Viruses Online (http://image.fs.uidaho.edu/vide/descr009.htm) (downloaded May 18, 2002) (11 pgs.).
Wagner et al., "Plant virus expression systems for transient production of recombinant allergens in *Nicotiana benthamiana*," *Methods: A Companion to Methods in Enzymology*, 32(3):228-232, 2004.
Wang et al., "Immunogenicity of Plasmodium *Yoelii merozoite* surface protein 4/5 produced in transgenic plants," *International Journal of Parasitology*, 38(1):103-110, 2007.
Webster et al., "Antigenic Structure and Variation in an Influenza Virus N9 Neuraminidase," *J. Virology*, 61:2910-2916, 1987.
Webster et al., "Measles virus hemagglutinin protein expressed in transgenic lettuce induces neutralizing antibodies in mice following mucosal vaccination," *Vaccine*, 24(17): 3538-3544, 2006.
Webster et al., "Protection of ferrets against influenza challenge with a DNA vaccine to the haemagglutinin," *Vaccine*, 12(16):1495-1498, 1994.
Williamson et al., "Human Immune Response to a Plague Vaccine Comprising Recombinant F1 and V Antigens," *Infect. Immun.*, 73(6):3598-608, 2005.
Williamson et al., "A single dose sub-unit vaccine protects against pneumonic plague," *Vaccine*, 19:566-71, 2000.
Williamson et al., "A new improved sub-unit vaccine for plague: the basis of protection," *FEMS Immunol. Med. Microbiol.*, 12:223-30, 1995.
Wilson et al., "Structure of the haemagglutinin membrane glycoprotein of influenza virus at 3 Å resolution," *Nature*, 289:366, 1981.
Winter and Milstein, "Man-made antibodies," *Nature*, 349:293, 1991.
Woo, "The Haematocrit Centrifuge Technique for the Diagnosis of African *Trypanosomiasis*," *Acta Tropica*, 27:384, 1970.
The World Health Organization Global Influenza Program Surveillance Network, Evolution of H5N1 Avian Influenza Viruses in Asia, Emerging Infectious Diseases, 11(10):1515-1521, 2005.
Yang et al., "Production and diagnostic application of monoclonal antibodies against influenza virus H5," *Journal of Virological Methods*, 162(1-2):194-202, 2009.
Yusibov et al., "An influenza N1 neuraminidase-specific monoclonal antibody with broad inactivating activity against H5N1 viruses," *Human Antibodies*, 16(1-2):33, 2007.

Yusibov et al., "An influenza N1 neuraminidase-specific monoclonal antibody protects animal against live challenge with homologous H5N1 virus," *Human Antibodies*, 17(1-2): 15, 2008.
Yusibov et al., "Antigens Produced in Plants by Infection with Chimeric Plant Viruses Immunize Against Rabies Virus and HIV-1," *Proc. Natl. Acad. Sci. USA*, 94:5784-5788, 1997.
Yusibov et al., "N-Terminal Basic Amino Acids of Alfalfa Mosaic Virus Coat Protein Involved in the Initiation of Infection," *Virology*, 208:405-407, 1995.
Yusibov et al., "Functional Significance of Three Basic N-Terminal Amino Acids of Alfalfa Mosaic Virus Coat Protein," *Virology*, 242:1-5, 1998.
Yusibov et al., "Purification, characterization, assembly and crystallization of assembled alfalfa mosaic virus coat protein expressed in *Escherichia coli*," *J. Gen. Virol.*, 77:567-573, 1996.
Yusibov et al., "Expression in plants and immunogenicity of plant virus-based experimental rabies vaccine," *Vaccine*, 20:3155-3164, 2002.
Zapata et al., "Engineering linear F(ab')2 fragments for efficient production in *Escherichia coli* and enhanced antiproliferative activity," *Prot. Eng.*, 8:1057, 1995.
Zumbach et al., "Antibodies Against Oncoproteins E6 and E7 of Human Papillomavirus Types 16 and 18 in Patients with Head-and-Neck Squamous-Cell Carcinoma," *International Journal of Cancer*, 85:815-818, 2000.
Advisory Action dated Jan. 15, 2010 for U.S. Appl. No. 11/706,568 (3 pgs.).
Communication dated Feb. 18, 2010 for EP Appln. No. 07750905.7 (2 pgs.).
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003969 (6 pgs.).
International Preliminary Report on Patentability dated Aug. 19, 2008 for Int'l. Appln. No. PCT/US07/003973 (6 pgs.).
International Preliminary Report on Patentability dated Mar. 17, 2009 for Int'l. Appln. No. PCT/US07/004103 (5 pgs.).
International Preliminary Report on Patentability dated Nov. 3, 2009 for Int'l. Appln. No. PCT/US08/061782 (7 pgs.).
International Preliminary Report on Patentability dated Jan. 12, 2010 for Int'l. Appln. No. PCT/US08/069860 (5 pgs.).
International Preliminary Report on Patentability dated Mar. 4, 2010 for Int'l. Appln. No. PCT/US08/073776 (6 pgs.).
International Preliminary Report on Patentability dated Mar. 29, 2011 for Int'l. Appln. No. PCT/US09/058640 (7 pgs.).
International Preliminary Report on Patentability dated Mar. 29, 2011 for Int'l. Appln. No. PCT/US09/058669 (12 pgs.).
International Search Report and Written Opinion dated Jun. 18, 2008 for Int'l. Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Aug. 3, 2007 for Int'l. Appln. No. PCT/US07/003973 (9 pgs.).
International Search Report and Written Opinion dated Aug. 7, 2007 for Int'l. Appln. No. PCT/US07/004103 (9 pgs.).
International Search Report and Written Opinion dated Oct. 21, 2008 for Int'l. Appln. No. PCT/US08/061782 (10 pgs.).
International Search Report and Written Opinion dated May 29, 2009 for Int'l Appln. No. PCT/US08/069860 (8 pgs.).
International Search Report and Written Opinion dated Apr. 24, 2009 for Int'l. Appln. No. PCT/US08/073776 (11 pgs.).
International Search Report and Written Opinion dated May 11, 2010 for Int'l. Appln. No. PCT/US09/058488 (20 pgs.).
International Search Report and Written Opinion dated Feb. 2, 2010 for Int'l. Appln. No. PCT/US09/058640 (13 pgs.).
International Search Report and Written Opinion dated May 19, 2010 for Int'l. Appln. No. PCT/US09/058669 (21 pgs.).
International Search Report and Written Opinion dated Jan. 27, 2011 for Int'l. Appln. No. PCT/US10/050693 (7 pgs.).
Notification of Defects in Patent Application dated Sep. 16, 2010 for Israel Patent Appln. No. 193391 (3 pgs.).
Office Action (non-final) dated Nov. 4, 2008 for U.S. Appl. No. 11/706,568 (7 pgs.).

Office Action (non-final) dated Jan. 6, 2009 for U.S. Appl. No. 11/706,568 (8 pgs.).
Office Action (final) dated Jul. 15, 2009 for U.S. Appl. No. 11/706,568 (7 pgs.).
Supplementary European Search Report dated May 5, 2010 for Appln. No. EP 07750784 (8 pgs.).
Supplementary European Search Report dated Oct. 8, 2009 for Appln. No. EP 07750950 (5 pgs.).
Supplementary European Search Report dated Jun. 9, 2010 for Appln. No. EP 08780572 (5 pgs.).

* cited by examiner

A

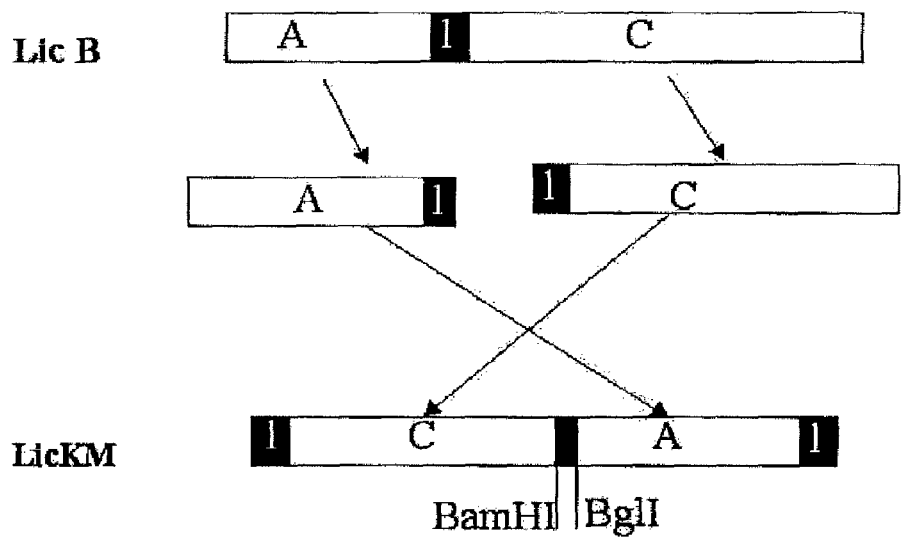

```
5'GG AAT TCA GGA ATG AGA GGA TCG CAT CAC CAT CAC CAT CAC gga tcc ATG GGC
GGT TCA TAT CCG TAT AAA AGC GGT GAA TAT CGT ACA AAA TCA TTT TTC GGA TAC
GGT TAT TAT GAA GTA AGA ATG AAA GCT GCC AAA AAC GTA GGA ATT GTT TCA TCT
TTC TTC ACT TAT ACA GGA CCT TCG GAC AAC AAT CCA TGG GAC GAA ATC GAT ATC
GAG TTT TTA GGA AAG GAC ACA ACT AAA GTT CAG TTC AAC TGG TAC AAA AAT GGA
GTC GGT GGA AAC GAG TAT TTG CAC AAT CTT GGA TTC GAT GCT TCC CAG GAT TTT
CAT ACA TAT GGA TTT GAA TGG AGG CCG GAT TAT ATA GAC TTC TAT GTT GAC GGC
AAA AAA GTT TAT CGT GGA ACC AGG AAC ATA CCT GTT ACT CCC GGC AAA ATT ATG
ATG AAT TTG TGG CCA GGA ATA GGA GTG GAT GAA TGG TTG GGA CGT TAC GAC GGA
AGA ACT CCT TTG CAG GCG GAG TAC GAA TAT GTA AAA TAC TAT CCT AAC GGT aga
tcc ATG GTG GTA AAT ACG CCT TTT GTT GCA GTG TTT TCG AAC TTT GAC TCC AGT
CAG TGG GAA AAA GCG GAT TGG GCG AAC GGT TCG GTG TTC AAC TGT GTT TGG AAG
CCT TCA CAG GTG ACA TTT TCG AAC GGT AAA ATG ATT TTG ACC CTT GAC AGG GAA
TAT aga tct 3'
```

ATGAGAGGATCGCATCACCATCACCATCACGGATCCGCATGCGAGCTCGGTACCCCGGGTCGAGGGCCC
ATGGTAAATACGCCTTTTGTTGCAGTGTTTTCGAACTTTGACTCCAGTCAGTGGGAAAAAGCGGATTGG
GCGAACGGTTCGGTGTTCAACTGTGTTTGGAAGCCTTCACAGGTGACATTTTCGAACGGTAAAATGATT
TTGACCCTTGACAGGGAATATGGCGGTTCATATCCGTATAAAAGCGGTGAATATCGTACAAAATCATTT
TTCGGATACCGGTTATTATGAAGTAAGAATGAAAGCTGCCAAAAACGTAGGAATTGTTTCATCTTTCTTC
ACTTATACAGGACCTTCGGACAACAATCCATGGACGAAATCGATATCGAGTTTTTAGGAAAGGACACA
ACTAAAGTTCAGTTCAACTGGTACAAAAATGGAGTCGGTGGAAACGAGTATTTGCACAATCTTGGATTC
GATGCTTCCCAGGATTTTCATACATATGGATTTGAATGGAGGCCGGATTATATAGACTTCTATGTTGAC
GGCAAAAAGTTTATCGTGGAACCAGGAACATACCTGTTACTCCCGGCAAAATTATGATGAATTTGTGG
CCAGGAATAGGAGTGGATGAATGGTTGGGACGTTACGACGGAAGAACTCCTTTGCAGGCGGAGTACGAA
TATGTAAAATACTATCCTAACGGTGTTCCGCAAGATAATCCTACTCCTACTCCTACGATTGCTCCTTCT
ACTCCGAGATCTATCTAGA

MRGSHHHHHHGSMGGSYPYKSGEYRTKSFFGYGYYEVRMKAAKNVGIVSSFFTYTGPSDNNPWDEIDIE
FLGKDTTKVQFNWYKNGVGGNEYLHNLGFDASQDFHTYGFEWRPDYIDFYVDGKKVYRGTRNIPVTPGK
IMMNLWPGIGVDEWLGRYDGRTPLQAEYEYVKYYPNGRSMVVNTPFVAVFSNFDSSQWEKADWANGSVF
NCVWKPSQVTFSNGKMILTLDREYRSI

MRGSHHHHHHGSACELGTPGRGPMVNTPFVAVFSNFDSSQWEKADWANGSVFNCVWKPSQVTFSNGKMI
LTLDREYGGSYPYKSGEYRTKSFFGYGYYEVRMKAAKNVGIVSSFFTYTGPSDNNPWDEIDIEFLGKDT
TKVQFNWYKNGVGGNEYLHNLGFDASQDFHTYGFEWRPDYIDFYVDGKKVYRGTRNIPVTPGKIMMNLW
PGIGVDEWLGRYDGRTPLQAEYEYVKYYPNGVPQDNPTPTPTIAPSTPRSI

Figure 1F

G
GGATCCTTAATTAAAATGCACCATCACCATCACCATGGCGGTTCATATCCGTATAAAAGCGGTGAATAT
CGTACAAAATCATTTTTCGGATACGGTTATTATGAAGTAAGAATGAAAGCTGCCAAAAACGTAGGAATT
GTTTCATCTTTCTTCACTTATACAGGACCTTCGGACAACAATCCATGGGACGAAATCGATATCGAGTTT
TTAGGAAAGGACACAACTAAAGTTCAGTTCAACTGGTACAAAAATGGAGTCGGTGGAAACGAGTATTTG
CACAATCTTGGATTCGATGCTTCCCAGGATTTTCATACATATGGATTTGAATGGAGGCCGGATTATATA
GACTTCTATGTTGACGGCAAAAAGTTTATCGTGGAACCAGGAACATACCTGTTACTCCCGGCAAAATT
ATGATGAATTTGTGGCCAGGAATAGGAGTGGATGAATGGTTGGGACGTTACGACGGAAGAACTCCTTTG
CAGGCGGAGTACGAATATGTAAAATACTATCCTAACGGTAGATCTGAATTCAAGCTTGTGGTAAATACG
CCTTTTGTTGCAGTGTTTTCGAACTTTGACTCCAGTCAGTGGGAAAAAGCGGATTGGGCGAACGGTTCG
GTGTTCAACTGTGTTTGGAAGCCTTCACAGGTGACATTTTCGAACGGTAAAATGATTTTGACCCTTGAC
AGGCAATATTGACTCGAGCTC

Figure 1G

H
MHHHHHHGGSYPYKSGEYRTKSPFGYGYYEVRMKAAKNVGIVSSFFTYTGPSDNNPWDEIDIEFLGKDT
TKVQFNWYKNGVGGNEYLHNLGFDASQDFHTYGFEWRPDYIDFYVDGKKVYRGTRNIPVTPGKIMMNLW
PGIGVDEWLGRYDGRTPLQAEYEYVKYYPNGRSEFKLVVNTPFVAVFSNFDSSQWEKADWANGSVFNCV
WKPSQVTFSNGKMILTLDREY

RECOMBINANT CARRIER MOLECULE FOR EXPRESSION, DELIVERY AND PURIFICATION OF TARGET POLYPEPTIDES

This application is a continuation of U.S. application Ser. No. 10/558,109, filed May 24, 2004, which is a National Phase entry under 35 U.S.C. §371 of PCT Application No. PCT/US2004/016452, filed May 24, 2004, which claims the benefit of U.S. Provisional Application No. 60/472,495, filed May 22, 2003, all of which applications are hereby incorporated by reference in their entirety.

FIELD OF THE INVENTION

The present invention is directed to the field of protein expression, purification and molecular biology. Specifically, the present invention is directed to a carrier protein expression in which a mature polypeptide of a thermostable enzyme is used as carrier molecule for production, recovery and delivery of target polypeptides. The carrier molecule is useful for the production of foreign sequences in different expression systems and hosts including plants and mammalian cell cultures.

BACKGROUND OF THE INVENTION

Vaccines are the most effective means for preventing and even eliminating infectious diseases. Although, there are a number of efficacious vaccines based on full pathogens, development of safer more potent and cost effective vaccines based on portions of pathogen (subunit vaccines) is important. During the last two decades several approaches to the expression (bacterial, yeast, mammalian cell culture and plant) and delivery (DNA, live virus vectors, purified proteins, plant virus particles) of vaccine antigens have been developed. All these approaches have significant impact on the development and testing of newly developed candidate vaccines. However, there is a need for improving expression and delivery systems to create more efficacious but safer vaccines with fewer side effects. Some of the desired features of future vaccines are (a) to be highly efficacious (stimulates both arms of immune system), (b) to have known and controlled genetic composition, (c) to have time efficiency of the system, (d) to be suitable for expression of both small size peptides and large size polypeptides, (e) to be suitable for expression in different systems (bacteria, yeast, mammalian cell cultures, live virus vectors, DNA vectors, transgenic plants and transient expression vectors), and (f) to be capable of forming structures such as aggregates or virus like particles that are easy to recover and are immunogenic.

Thus, there is a need for novel carrier molecules for engineering, development and delivery of efficacious subunit vaccines. These carrier molecules should provide advantages and flexibility for: expressing commercially sufficient quantities of target polypeptide in different systems, economical recovery of target polypeptides from source material, accommodating different size (4 amino acids and higher) polypeptides, accommodating tandem repeats of target polypeptides, providing enhanced immune function, use as a high throughput screening tool, and use as a delivery tool for vaccine antigens and disease markers.

SUMMARY OF THE INVENTION

In the present invention, a novel recombinant protein has been discovered. It will serve as a carrier molecule for expression and recovery of useful target polypeptides for use as therapeutic or preventative agents against infectious diseases or even cancer. The carrier molecule discovered herein can accommodate polypeptides of varying sizes (4 amino acids to a 100 kD protein and higher) (target polypeptides) and can be expressed in different systems. The target polypeptides can be vaccine antigens In a general aspect, the present invention provides a recombinant carrier molecule having a modified mature polypeptide of a thermostable enzyme lacking one or more segments of amino acids or a substantially complete mature polypeptide of the thermostable enzyme suitable for fusing to a heterologous polypeptide at each of N-terminus and C-terminus of the mature polypeptide, and optionally in the loop region. The modified mature polypeptide and substantially complete mature polypeptide retain their thermostability and/or enzyme activity. The mature polypeptide of is modified in that it lacks a loop region or has a disrupted loop region, or has at least one restriction site in the loop region not naturally present in the wild type thermostable enzyme.

In one preferred embodiment, the carrier molecule discovered herein is based on lichinase B (licB) gene from *Clostridium thermocellum* (accession: X63355, [gi:40697]). The inventors discovered that this thermostable bacterial enzyme can be used as a carrier molecule for producing target polypeptides. It has loop structure exposed on the surface that is located far from the active domain. It has been discovered by the present inventors that this loop structure can be used for the insertion of target polypeptides. The target polypeptides can be expressed as N or C terminal fusions or internal fusions and/or as inserts into loop structure. Modified protein is expressed and characterized for any of the parameters such as thermostability, pH and temperature conditions for optimal activity. Engineered protein retained its pH and temperature conditions for optimal activity. It also did not change its thermostability at 65° C.

Accordingly, the present invention discloses a recombinant molecule derived from a thermostable enzyme for use as a carrier for various heterologous target polypeptides (e.g., vaccines, hormones, anticoagulants, immunoglobulins, interferons, interleukins, hematopoietic growth factors, etc). In specific embodiments, it discloses Rec LicB and LicKM. The carrier protein (i.e., modified or engineered rec LicB or LicKM linked to one or more heterologous target polypeptides) is a fusion protein and it may be expressed in either prokaryotic or eukaryotic systems. Specifically it has been found that these carrier molecules can accommodate from small to a large size polypeptides of up to 100 kD and more, can accommodate tandem repeats of the same polypeptide, can be expressed in different systems, including bacterial, yeast, baculovirus, mammalian cell cultures, plants, DNA and virus vectors, can provide economic advantages for recovery of target product due to their thermostability or capacity to form aggregates, can be used as high throughput system for screening target polypeptides; antigens, disease markers or other therapeutic polypeptides.

The present invention also discloses a method for expressing peptides as fusion proteins, by using a recombinant mature polypeptide of a thermostable enzyme as the carrier for heterologous polypeptide(s) and using the peptide expression methods described herein.

BRIEF DESCRIPTION OF THE DRAWINGS

FIG. 1C shows the construction of Rec LicB from the wildtype LicB. The Rec LicB consists of mature protein without cellulosome binding domain. Target sequences can be fused to N and C terminus as well as into loop structure using BamHI and BglII restriction sites.

FIG. 1D shows the nucleic acid sequence for engineered molecule Rec LicB (SEQ ID NO:2).

FIG. 1E shows a sequence of amino acids (SEQ ID NO:3) encoded by LicKM nucleic acid (SEQ ID NO:1).

FIG. 1F shows a sequence of amino acids (SEQ ID NO:4) encoded by Rec LicB (SEQ ID NO:2).

FIG. 1G shows the nucleic acid sequence for a variant of LicKM carrier molecule (SEQ ID NO:5). It also has a KpnI restriction site created at the 5' end and XhoI restriction site created at the 3' end and BamHI/Bgl site in the loop region.

FIG. 1H shows a sequence of amino acids (SEQ ID NO:6) encoded by a variant of LicKM carrier molecule (SEQ ID NO:5).

The cloning was done in 2 steps by PCR. Using primers shown in FIG. 1 legend, 2 subclones, A and C were created. Then the sequences encoding GFP were PCR amplified (during PCR at the 5' and 3' ends, BamHI and BglII restriction sites were incorporated, respectively). Later, using the introduced BamHI and BglII sites, the 3 fragments were ligated as A-GFP-C to obtain LicB-GFP. Primers for GFP were:
Plus: 5' gcag gga tcc atg gtg agc aag ggc gag3' (SEQ ID NO:7)
Minus: 5' gcag aga tct ctt gta cag ctc gtc cat3' (SEQ ID NO:8)

Figure 3:
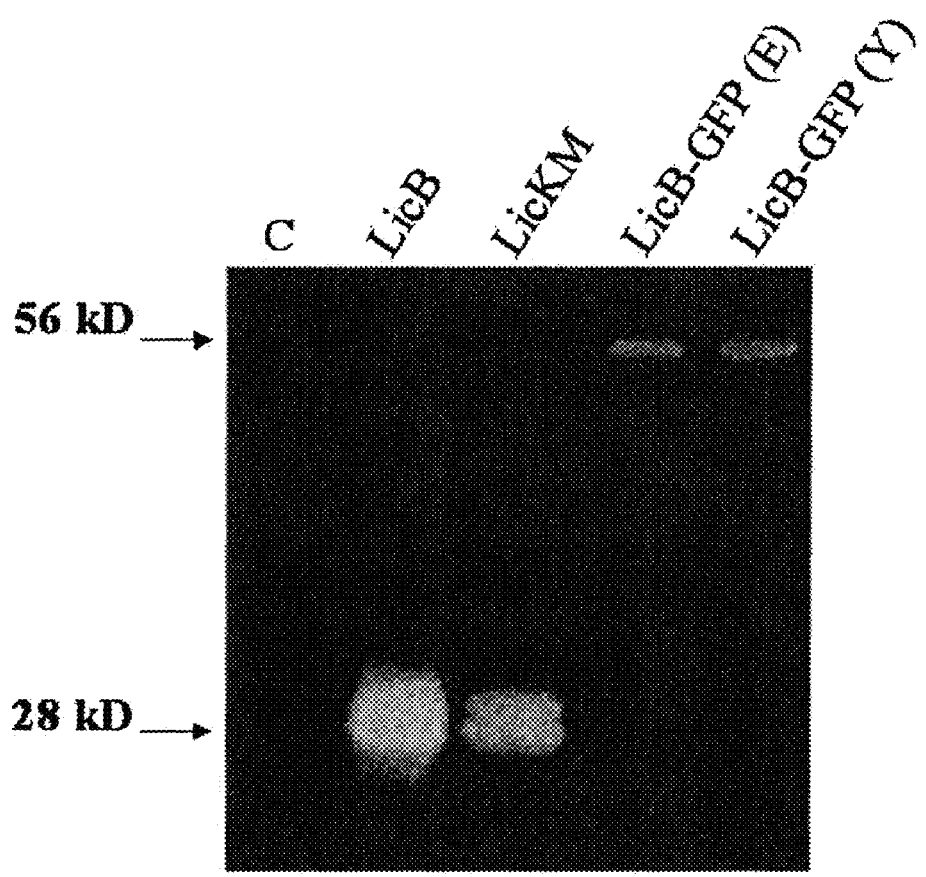

FIG. 3. Zymogram of lichenase activity in bacterial and yeast extracts detected in the presence of 0.1% lichenan as substrate. Proteins were separated in 12% PAGE. The gel was loaded with proteins extracted from *E. coli* strain XL-1 blue [C control, LicB (wild type), LicKM (engineered carrier molecule) and recombinant LicB-GFP (E)] and *Saccharromyces cerevisiae* strain YPH 857 (LicB-GFP (Y)).

Figure 4:
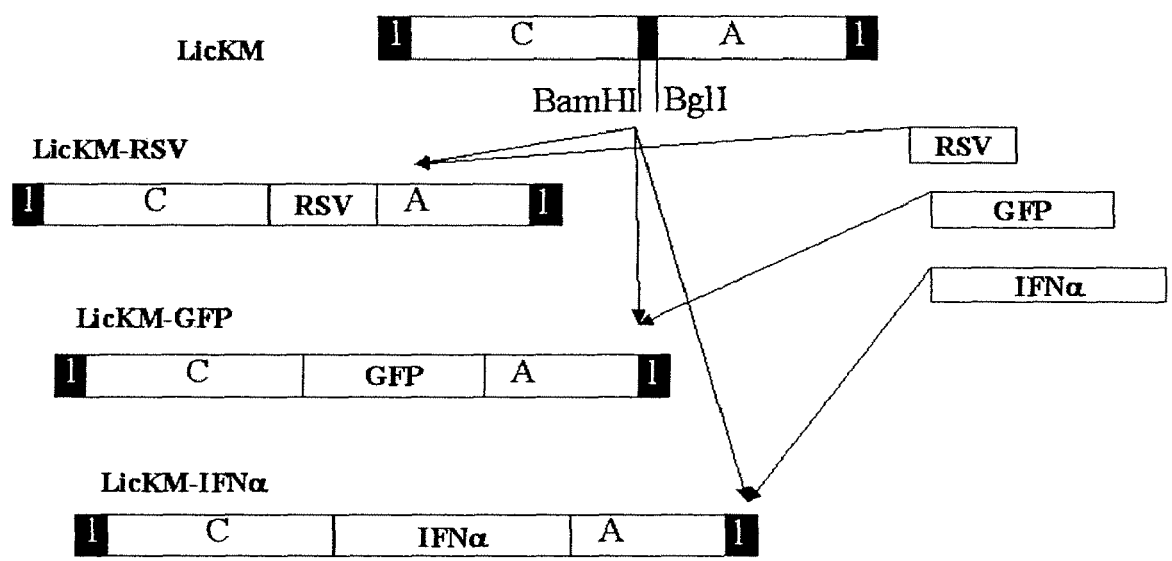

FIG. 4. Schematic representation of cloning of target polypeptides in engineered carrier molecule LicKM. DNA fragments encoding target polypeptides from respiratory syncytial virus (RSV) G protein, green fluorescent protein (GFP) from jelly fish, and human interferon α (IFNα) were PCR amplified and inserted into open reading frame of LicKM.

Figure 5:
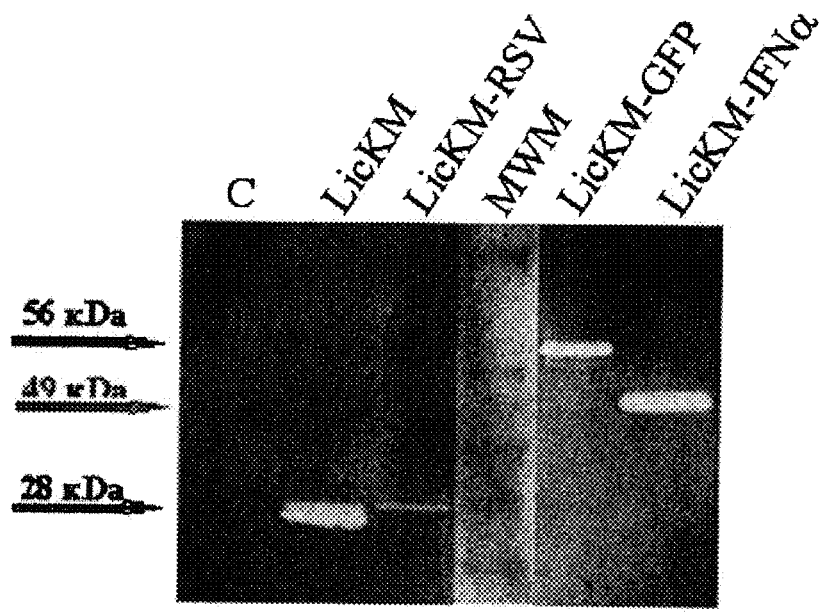
Figure 5:
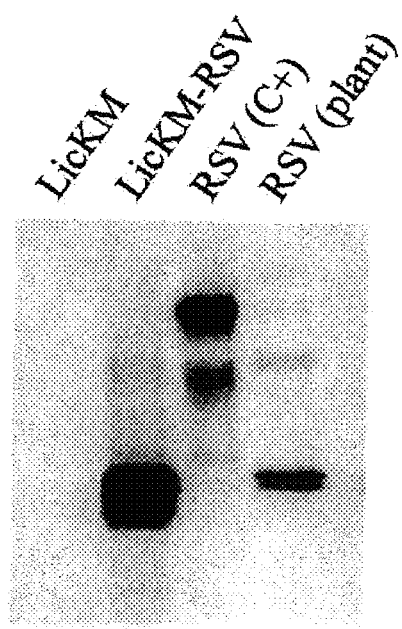

FIG. 5. A is zymogram of lichenase activity in bacterial extracts detected in the presence of 0.1% lichenan as substrate. Proteins were separated in 12% PAGE. The gel was loaded with proteins extracted from *E. coli* strain XL-1 blue. C is a negative control. LicKM is engineered carrier molecule. LicKM-RSV, LicKM-GFP, and LicKM-IFNα are engineered proteins containing respective target polypeptide. B shows the results of Western blot analysis. Proteins were separated in 12% PAGE, electroblotted onto nylon membrane and reacted with monoclonal antibodies specific for peptide from RSV G protein. Antibodies reacted with LicKM-RSV, RSV positive control (RSV (C+)) and plant virus coat protein containing identical peptide (RSV (plant)). Extracts from LicKM that did not contain target peptide had no specificity to RSV antibodies.

Figure 6:
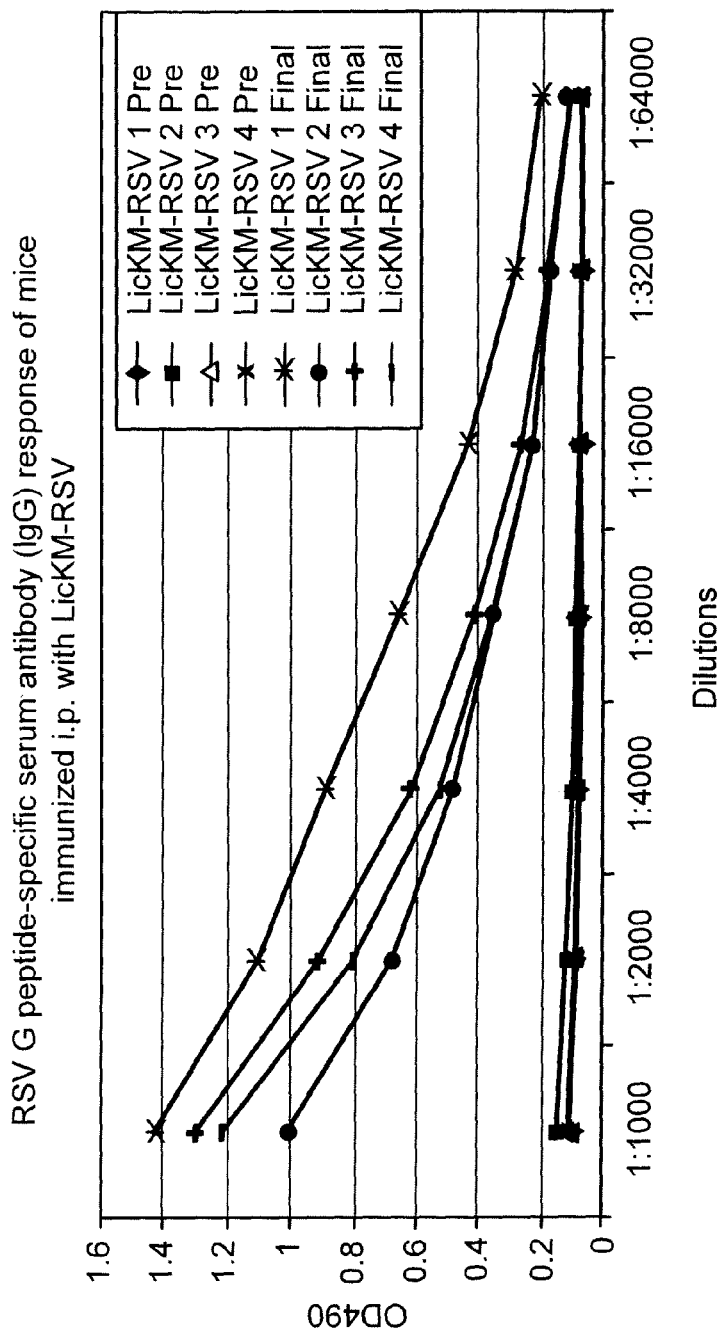

FIG. 6. RSV G peptide-specific serum antibody (IgG) response of mice immunized i.p. with LicKM-RSV. Serum antibody responses were measured by ELISA on plates coated with recombinant AlMV particles containing identical peptide (amino acids 171 to 191) from RSV G protein. Data represent $OD_{490}$ values obtained using preimmune (LicKM-RSV Pre) and sera after third dose (LicKM-RSV Final) of antigen. Numbers 1, 2, 3, and 4 indicates individual animals.

Figure 7:
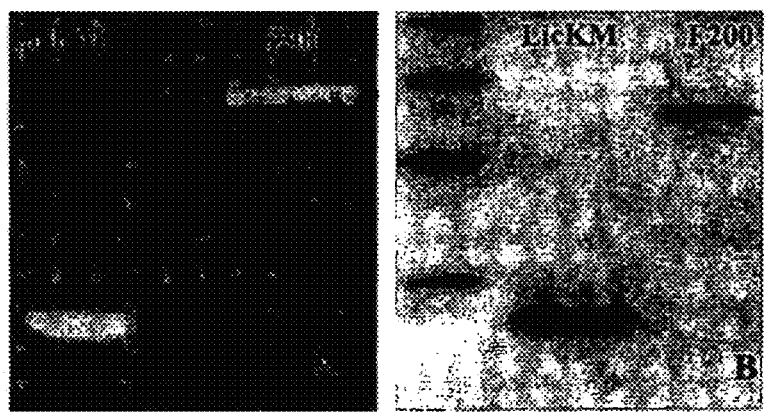

FIG. 7. Detection of LicKM-F200 enzymatically (A) and serologically (B) by Western analysis. Proteins were separated in 12% PAGE. A is zymogram of lichenase activity in plant extracts detected in the presence of 0.1% lichenan as substrate. LicKM-F200 (F200) reacted with antibodies specific to LicKM. Both methods detected protein of expected size (47 kD).

Figure 8:
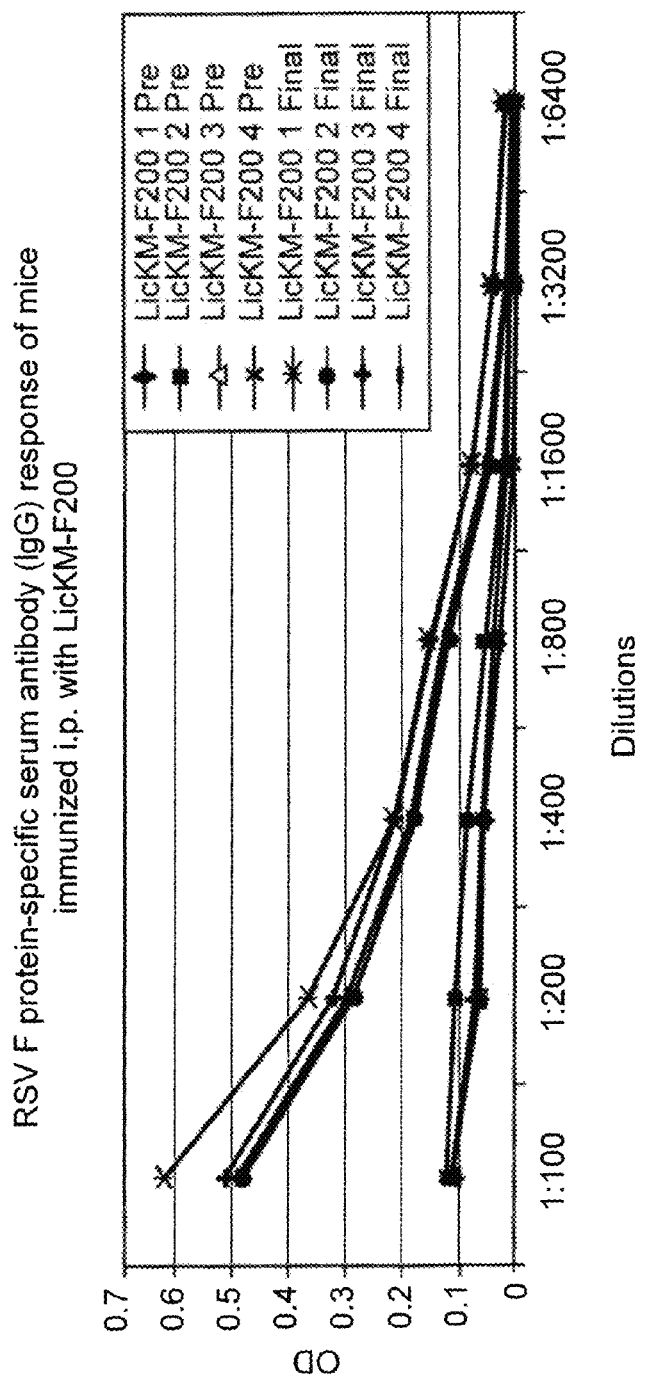

FIG. 8. RSV F protein-specific serum antibody (IgG) response of mice immunized i.p. with LicKM-F200. Serum antibody response was measured by ELISA using plates coated with inactivated RSV Long strain. Data represent $OD_{490}$ values obtained using preimmune (LicKM-F200 Pre) and sera after third dose (LicKM-F200 Final) of antigen. Numbers 1, 2, 3, and 4 indicates pre and post-immune serum samples collected from individual animals.

Figure 9:
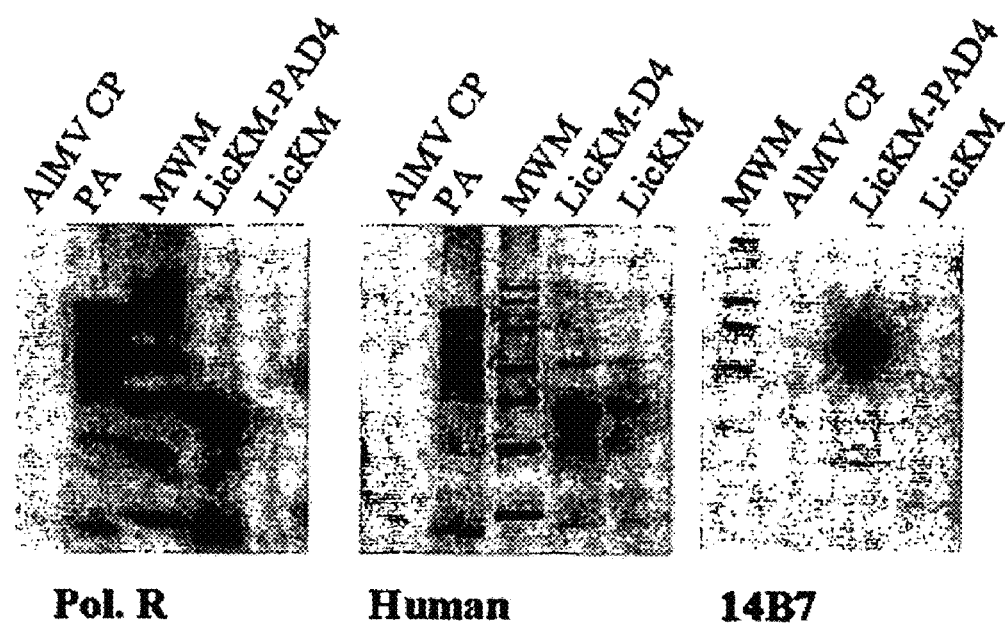

FIG. 9. Western blot analysis of recombinant LicKM-PAD4. Proteins were separated electrophoretically (12% SDS-polyacrylamide gel), transferred to a membrane, and reacted with different antibodies. All antibodies specific to PA, including monoclonal antibody 14B7 recognized the LicKM-PAD4 or control PA. AlMV CP or LicKM, used as negative controls, did not react with any of antibodies.

Figure 10:
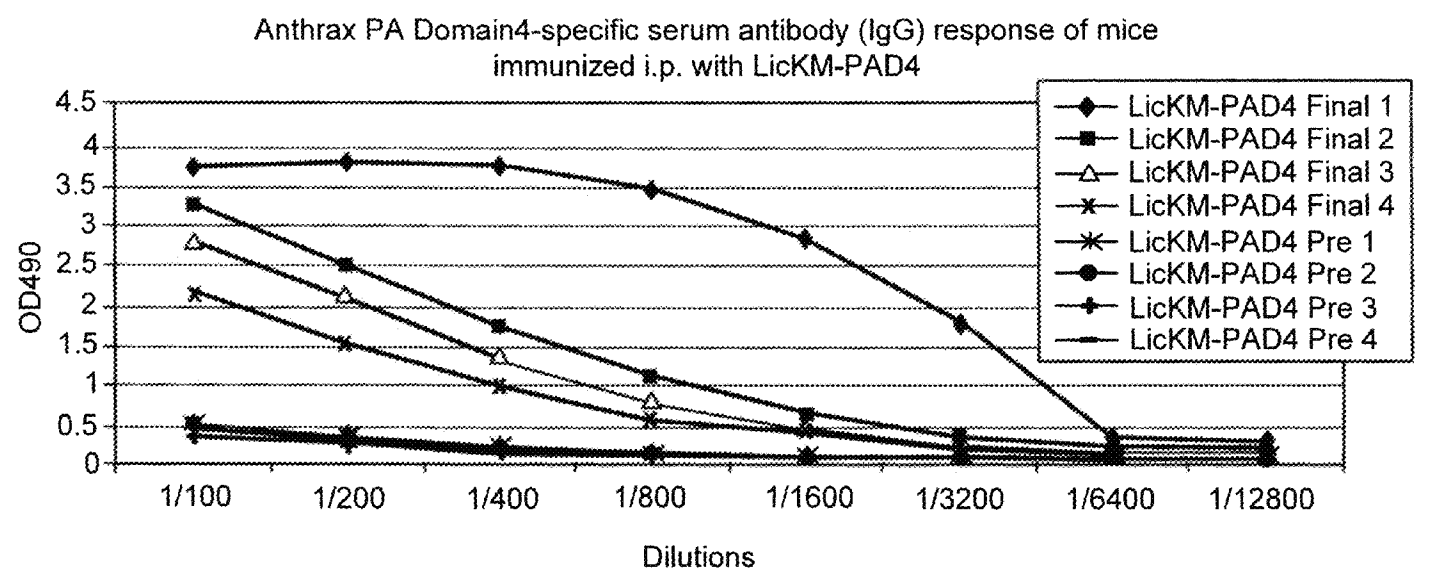

FIG. 10. Anthrax PA Domain4-specific serum antibody (IgG) response of mice immunized i.p. with LicKM-PAD4. Serum antibody response was measured by ELISA using plates coated with recombinant PA. Data represent $OD_{490}$ values obtained using preimmune sera (LicKM-PAD4 Pre) and sera after the third dose (LicKM-PAD4 Final) of antigen.

DETAILED DESCRIPTION OF THE INVENTION

The present invention is based on the discovery that recombinant forms of certain thermostable enzymes can be used as carriers or carrier molecules for expression, stabilization, display, purification and/or delivery of various genetically fused polypeptides of interest (target polypeptides) such as vaccine antigens, enzymes, antibodies (single chain) and therapeutic polypeptides.

The present invention discloses, among other things, (i) a variety of thermostable carrier molecules derived from thermostable enzymes and heterologous polypeptide-containing carrier proteins, (ii) nucleic acid constructs, which can encode recombinant carrier molecules and carrier proteins of the invention, and cells and organisms transformed with carrier protein expression constructs, (iii) methods for producing vaccine antigens in cells and organisms; (iv) methods for stimulating an immune response in animals and humans, the immune response being directed toward a carrier protein, specifically toward target antigen of the present invention, (v) methods for inducing humoral and cellular responses against infectious agents using a carrier fusion protein described below, and (vi) methods for producing various industrial enzymes (other than the thermostable enzymes) and therapeutic proteins.

Thermostable enzymes are polypeptides that function at or greater than 60° C. A number of thermostable enzymes that are known in the art, can be obtained from thermophilic organisms found in hot springs, volcanic regions etc. and used as carrier molecule. Lichinase B (LicB) protein. from *Clostridium thermocellum* is one such example of thermostable enzymes. The present invention encompasses recombinant carrier molecules derived from thermostable enzymes from natural sources, i.e., any microbial sources (bacteria and fungi) or synthetic sources. Examples of such enzymes are lichenase B (Piruzian et al., 2002, Mol Genet Genomics, 266: 778-786), xylanase and xylosidase from *Bacillus thermactarantis* that are active at 80° C. (Calandrelli et al., Res. Microbiol. 2004, 155(4):283-289), formiltransferase from *Methanopyrus kandleri* (Shima et al., Biochem Soc. Trans., 2004, 32:269-272), Taq polymerase, alpha-amylase from *Asperigillus tamarii* (Moreira et al., J. Basic Microbiology, 2004, 44:29-35) or beta-glucosidase from *Thermus nonproteolyticus* (Wang et al., J. Bacteriology, 2003, 185:4248-55).]

The molecular structure of wild type lichenase B (LicB) gene and protein are well known to one skilled in the art (See, GenBank Accession Number X63355). The wild type LicB has 27 amino acids long signal peptide and 235 amino acids long mature peptide. Mature peptide has a catalytic domain and 12 amino acid (a.a. 82-94) loop region. LicB is member of glycosyl hydrolases (hydrolases βglucan in position 1-4) and is a thermostable protein. Optimum temperature for enzymatic activity is between 65-70° C. According to 3D structure of the wild type Lic B, the N and C terminal regions of protein are co-localized in close proximity from active domain. The external loop is positioned far from active domain and exposed on the surface.

The terms "carrier" "carrier molecule" "recombinant carrier molecule" used interchangeably herein refer to a recombinant thermostable enzyme used for expression, stabilization, display, purification and/or delivery of heterologous polypeptide(s) translationally fused to the recombinant thermostable enzyme. The thermostable enzyme is recombinant in the sense that it is a modified mature polypeptide of a selected wild-type thermostable enzyme. The modified mature polypeptide lacks one or more portions (or strings or segments) of amino acids but the modified mature polypeptide must retain its enzymatic activity or thermostability. For example, the mature polypeptide may lack a loop region or a string of 5 or more amino acids. Further, for example, the loop region of the mature polypeptide is disrupted (i) by introducing few amino acids coded for by at least one unique restriction site, and/or (ii) by splitting the gene at its loop region to generate two portions (N and C-terminal portions) of the mature polypeptide, which two portions are then reengineered (circularly permutated) into a single reading frame from C-terminus to N-terminus. As a result, the original C-terminal portion remain fused upstream of the original N-terminal portion. During this reengineering, unique restriction site(s) may be incorporated at 5' and 3' ends as well as internally including at the site corresponding to the fusion site. be recombined so that the recombined polypeptide is flanked at N and C-termini by the disrupted loop portions of or a string of 5 or more amino acids.

In the context of the present invention, the unique restriction site means the one introduced into the nucleic acid during the engineering process and it is the only site present in the engineered nucleic acid.

Alternatively, the thermostable enzyme is recombinant in the sense that it is a complete or substantially complete mature polypeptide of a selected wild-type thermostable enzyme and the encoding recombinant nucleic acid sequence has unique restriction sites at the 5' end and at the 3' end, and optionally in the loop region for fusion of a heterologous polypeptide at each of N-terminus and C-terminus, and in the loop region. Upstream of the unique restriction site at the 5' end, an ATG codon is incorporated. Downstream of the unique restriction site at the 3' end, a stop codon is incorporated. One skilled in the art would know how to create a carrier molecule of the invention by making manipulations at the nucleic acid level.

In one embodiment, the wild type licB protein is modified such that it lacks signal peptide and cellulosome binding domain to create a recombinant licB carrier molecule with unique cloning sites introduced into the loop region.

Referring to LicB shown in FIG. 1C, the wild type LicB consists of a leader peptide (27 amino acids, indicated as Lp), mature polypeptide (235 amino acids symbolically divided into 3 regions (A, 1 and C), Pro-thr-box and cellulosome binding domain designated as C-BD. Whereas the Rec LicB contains only the open reading frame for mature protein (235 a. a.) that lacks sequences for Lp and C-BD. In some embodiments, however, the C-BD is retained.

In another embodiment, the wild type licB protein is modified so that certain regions of it are deleted together and certain regions of it are shuffled or swapped to create a recombinant carrier molecule. Specifically, the N and C terminal regions (designated herein as A and C, respectively) are circularly permutated. For example a recombinant carrier molecule referred to herein as LicKM can be created as follows. As described in the brief description of FIG. 1, sets of primers are used to obtain fragments A and C which subsequently are ligated as C-A, fusing the fragment A into the open reading frame of fragment C. LicKM maintains both enzymatic activity and thermostability similar to that of wild type.

The carrier molecules recLicB and LicKM are merely preferred and exemplary molecules of the enzyme. It should be readily apparent that a number of variant or equivalent recLicB or LicKM carrier molecules (and nucleotide sequences coding for equivalent molecules) having the same or similar or higher thermostability can be prepared by mutating these preferred carrier molecules, for example, by deletion, addition or substitution of amino acids or by directed evolution or gene shuffling of these molecules. One skilled in the art would know how to carry out such alterations to arrive at equivalent or variant LicB-based carrier molecules. A variant carrier molecule, as the term used herein, will have the same ability, like that of recLicB or LicKM, to facilitate at least one of expression, stabilization, display, purification or delivery of a heterologous polypeptide fused to the molecule.

A variant or equivalent carrier molecule will have a degree of amino acid similarity or identity with the exemplified preferred molecule (e.g., LicKM or Rec LicB). This amino acid similarity or identity will typically be greater than 60%, preferably be greater than 75%, more preferably greater than 80%, yet more preferably greater than 90%, and can be greater than 95%. The amino acid similarity or identity will be highest in critical regions of the carrier molecule that account for the molecule's thermostability or are involved in the determination of three-dimensional configuration which ultimately is responsible for its carrier function. In this regard, certain amino acid substitutions are acceptable and can be expected if these substitutions are in regions that are not critical to activity or are conservative amino acid substitutions which do not affect the three-dimensional configuration of the molecule. Conservative substitutions whereby an amino acid of one class (non-polar such as Ala, Val, Leu, Ile, Pro, Met, Phe, Trp; uncharged polar such as Gly, Ser, Thr, Cys, Tyr, Asn, Gln; basic such as Lys, Arg, His; or acidic class such as Asp, Glu) is replaced with another amino acid of the same class so long as the substitution does not materially alter the thermostability or three-dimensional configuration. In some instances, non-conservative substitutions can also be made. The critical factor is that these substitutions must not significantly detract from the ability of "variant carrier molecule" to facilitate at least one of expression, stabilization, display, purification or delivery of a heterologous polypeptide.

The term "carrier fusion protein or carrier protein" as used herein generally refers to a chimeric fusion polypeptide or protein wherein one more heterologous polypeptides are fused to the carrier molecule.

The general architecture of the carrier protein can be, for example, any of the following:
$NH_2$-carrier molecule-heterologous polypeptide-COOH
$NH_2$-tag-cleavage site-carrier molecule-heterologous polypeptide-COOH
$NH_2$-carrier molecule-cleavage site-heterologous polypeptide-COOH
$NH_2$-tag-carrier molecule-cleavage site-heterologous polypeptide-COOH
$NH_2$-tag-cleavage site-carrier molecule-heterologous polypeptide-COOH The carrier molecule may also have an internal fusion, in which case the heterologous polypeptide is flanked on either side by a segment of the recombinant carrier molecule. The carrier protein exhibits a high degree of thermotolerance (at least at about 60° C.) which facilitates separation of the fusion protein from all other host cell proteins, nucleic acids, pyrogens, and the like after subjecting the lysate to heat and/or centrifugation. Fusion of heterologous polypeptide(s) either at N-terminus or C-terminus or internally) of a carrier molecule may not result in loss of enzymatic activity and thermostability.

A tag may also be linked to the carrier molecule or carrier protein as a tool for purification. The tag will serve as an additional tool for purification of the carrier molecule or carrier protein. The tag may also serve as fall back tool for purification. The tag refers to a peptide used for facilitating purification of a fusion protein prepared through expression by gene recombination. It is preferred that the bonding between a tag and a substance capable of binding thereto is reversible. The tag can be, for example, glutathione S-transferase with affinity for glutathione, a peptidic sequence of histidine residues where histidine has an affinity for a metal, and the like known in the art. In one preferred embodiment of the invention, such a tag is His His His His His His (SEQ ID NO:9) (i.e., $His_6$). In the present invention, one more linker sequences may be positioned in the carrier protein as needed.

As used herein, the term "heterologous polypeptide or protein" refers to a polypeptide or protein of interest (for therapeutic, diagnostic or preventative use) that is encoded by nucleic acid introduced into a host cell. The term heterologous polypeptide or protein does not include a thermostable enzyme or domains of a thermostable enzyme or its signal peptide. The heterologous polypeptide for purposes of this invention denotes a polypeptide of up to 100 kDa and higher and it generally refers to a polypeptide which is not endogenous to the host selected, although this definition will also include endogenous peptides in cases in which overexpression of such is desired. In addition, heterologous polypeptide will also exhibit some form of useful activity, typically either antigenic activity for use in recombinant vaccines and/or immunological assays or other biological activity (for example as a peptide hormone, biological marker etc).

The heterologous polypeptides include growth factors, cytokines, ligands, receptors and inhibitors, as well as antigenic determinants and antibodies. Heterologous proteins may also include enzymes such as hydrolases including carbohydrases, and lipases. Representative polypeptides within the scope of the invention include, without limitation, GFP, IFNα, antigens (or epitopes) such as from tetanus toxin, anthrax, measles virus, *Mycobacterium tuberculosis*, plague, and monoclonal antibodies specific for RSV, insulin, and the like.

In addition other peptides or proteins (or fragments thereof) such as epitopes from cytokines, e.g., interleukin-2 (IL-2), or granulocyte-macrophage colony stimulating factor (GM-CSF) or peptides containing both T cell and B cell epitopes may also be used to recruit various effector systems of the immune system, as required. For example, based upon the available nucleotide sequences of the target pathogen, one can clone computer generated open reading frames, express the target polypeptides in an appropriate system and screen them using material from infected individuals. Target polypeptides selected based on their immunoreactogenicity can be used for developing vaccine candidates, therapeutic or diagnostic reagents. The screening could provide highly time efficient and potent method and would be particularly important if one has to keep pace with emerging pathogens or disease out brakes such as SARS. Further, the carrier molecule can be used to determine appropriate vaccine antigens for developing efficacious vaccine against pathogens such as SARS, tuberculosis as well as subunit vaccines (e.g., against hepatitis B using surface antigen).

One or more cleavage sites can be introduced between the carrier molecule and the heterologous polypeptide depending on the location of the heterologous polypeptide in the carrier protein. This can facilitate further purification of the target polypeptides. It may also provide advantages over current protein synthesis methodologies, which result in much reactant and solvent toxic waste which must be disposed of.

For example, any of a number of prior art known cleavage sites specific to proteases or other such enzymes or chemicals useful in the efficient hydrolysis of peptide bonds may be introduced. Proteases that are active both as endo- and exopeptidases are known in the art. For example, protease specific cleavage site can be introduced into a recombinant LicKM carrier protein such that the LicKM carrier molecule has at its N-terminus a poly His tag and at its C-terminus the cleavage site followed by a target polypeptide such as an antigenic determinant and/or a therapeutic polypeptide of interest (e.g., interferon).

In some embodiments, for improving qualitative and quantitative parameters of target polypeptides, secretory signal sequences may be added. The use of leader sequences or secretory signal sequences are only optional, not necessary, for practicing the present invention. For example, one can construct recombinant vectors containing carrier protein with a leader sequence such as to direct the secretion of heterologous proteins into the medium used to culture various host cells.

Such a system would enable homogenous synthesis of the recombinant protein and the system would allow easy scaling-up and subsequent downstream processing, for example, purification. Such modifications have been made to a number of proteins known in the art.

The heterologous polypeptides can be fused to the carrier molecule framework as outlined above, whether at a single location or non-contiguous locations. Generally speaking, in the context of carrier proteins as vaccines, heterologous polypeptides or a sequence of amino acids containing one or more epitopes (i.e., epitope-containing segments having two or more identical or non-identical epitopes), which can stimulate an immune response that protects or prevents against an infectious disease or allergic reactions are candidate polypeptides. The use of an epitope-containing segment in which two or more distinct epitopes are displayed is preferred when attempting to create bifunctional antibodies for experimental, diagnostic or therapeutic uses. The heterologous polypeptides may contain epitopes that can be B cell epitopes, T cell epitopes or a mixture of B and T cell epitopes. In some contexts, preferred epitopes are B-cell epitopes which are known to be a target for neutralizing antibodies.

A preferred embodiment of the present invention relates to a carrier protein having the recombinant carrier molecule fused to two or more non-contiguous epitope-containing heterologous polypeptide segments. The non-contiguous locations where fusion is appropriate are internal locations within the carrier protein moiety including the loop region, or at the N- or C-terminus of the recombinant carrier molecule.

It has been found in the present invention that insertions and substitutions can be made within these loop regions without disrupting the integrity of the carrier molecule or abolishing the features which make the recombinant thermostable enzymes a useful carrier for the delivery expression various polypeptides or display of epitope containing heterologous polypeptides. Insertions and substitutions within these loop regions tend not to alter the relationships between the prominent structural features of the carrier molecule. One skilled in the art would know how to create a carrier protein of the invention by making manipulations at the nucleic acid level.

In some embodiments, the carrier protein will have cleavage sites such that the heterologous polypeptides fused to the C-terminus, N-terminus and/or internally of a recombinant carrier molecule of the invention can be cleaved off by specific proteases in vivo or in vitro. This allows the peptide to be administered to a cell as part of a larger fusion protein which is both easier to purify and handle as compared to free heterologous polypeptide. Following cellular uptake, the heterologous polypeptide attached to the carrier molecule can be cleaved from the molecule.

One skilled in the art would know how to create a carrier protein of the invention by making manipulations at the nucleic acid level. Construction of suitable vectors containing the desired coding and control sequences employs standard ligation and restriction techniques which are well understood in the art. Isolated plasmids, DNA sequences, or synthesized oligonucleotides are cleaved, tailored and religated in the form desired. Virus vectors such as plant, insect and mammalian virus vectors or bacterial plasmids can be used as vectors.

As representative examples of expression vectors can be viral particles, plasmids, cosmids, bacterial artificial chromosomes, viral DNA (e.g. vaccinia, adenovirus, foul pox virus, pseudorabies and derivatives of SV40), yeast plasmids, yeast artificial chromosomes, and any other vectors specific for specific hosts of interest (such as bacteria, yeast and other fungi, plants, etc.) Thus, for example, the DNA may be included in any one of a variety of expression vectors for expressing the recombinant carrier protein. Large numbers of suitable vectors are known to those of skill in the art, and are commercially available. The following vectors are provided by way of example; Bacterial: pQE70 (Qiagen), pBluescript SK, pBluescript KS (Stratagene); pTRC99a, pRIT2T (Pharmacia); Eukaryotic: pWLNEO, pXT1, pSG (Stratagene) pSVK3, pSVLSV40 (Pharmacia). Any other plasmid or vector may be used as long as they are replicable and viable in the host.

The recombinant DNA capable of encoding carrier protein may be inserted into the vector by a variety of procedures. In general, the DNA sequence is inserted into an appropriate restriction endonuclease site(s) by procedures known in the art.

The DNA sequence in the expression vector is operatively linked to an appropriate expression control sequence(s) or a promoter to direct mRNA synthesis. Promoters used in the present invention can be ubiquitous or constitutive and/or tissue specific promoters from prokaryotic and eukaryotic organisms. Examples of constitutive promoters are CaMV 35S promoter, the nopaline synthase promoter, the octopine synthase promoter, the ribulose-1,5-bisphosphate carboxylase promoter, Act1, SAM synthase promoter, and Ubi promoter and the promoter of the chlorophyll a/b binding protein. Examples of tissue specific promoters are potato protease inhibitor II (pin2) gene promoter, napin gene promoter, cruciferin gene promoter, beta-conglycinin gene promoter, phaseolin gene promoter, zein gene promoter, oleosin gene promoter, acyl carrier protein stearoyl-ACP desaturase gene promoter, a fatty acid desaturase gene promoter, glycinin, Bec4 and promoters from a number of nodule genes. A number of such promoters are known in the art. Inducible promoters that specifically respond to certain chemicals (copper etc.) or heat-shock (HSP) are also contemplated. In addition, the promoters also include artificial sequences designed to function as promoters. Selection of the appropriate vector and promoter is well within the level of ordinary skill in the art. The expression vector also contain other appropriate control sequences or other regions for facilitating transcription and translation and selection.

The expression vector may be introduced into a suitable host The host cell can be a eukaryotic cell, such as a mammalian cell, plant cell or a yeast cell, or the host cell can be a prokaryotic cell, such as a bacterial cell. Plant and animal cell cultures can also be used to produce carrier proteins of the invention. The selection of an appropriate host is deemed to be within the scope of those skilled in the art from the teachings herein. Preferred host cells are plant cells and organisms are plants. Introduction of the construct into the host cell can be effected by transformation, calcium phosphate transfection, DEAE-Dextran mediated transfection, or electroporation or other methods known in the art.

Depending on the host cell used, transformation is accomplished using standard techniques appropriate to such cells. The calcium treatment employing calcium chloride, which is known in the art, can be used. for prokaryotes or other cells which contain substantial cell wall barriers. Transformations into yeast are carried out according to the methods known in the art. For mammalian cells without cell walls electroporation or DNA uptake methods can be used. Insect cells known and routinely used for protein expression purposes are also used as host cell in the present invention. Infection with *Agrobacterium tumefaciens* is used for certain plant cells. Accordingly, in the methods of the invention, plant of interest is transformed with a vector containing the carrier protein of interest to produce a transgenic plant. *Agrobacterium*-based transformation methods may be used to produce transgenic plants. Several other methods for stable transformation of plants are available in the art (see, Piruzian et al., 2002, Mol Genet Genomics 266:778-786, which is incorporated herein by reference). In the present invention, the RecLicB and LicKM constructs containing several target antigens, including RSV peptide and hepatitis B surface antigen can be expressed in plants.

The carrier protein of the present invention may also be expressed from a suitable viral vector after infecting a host plant with the selected viral vector. Recombinant viral vectors can be constructed by manipulating the genomic component of the wild-type viruses. Preferred viruses are RNA containing plant viruses. Although many plant viruses have RNA genomes, it is well known that organization of genetic information differs among groups. Thus, a virus can be a mono-, bi-, tri-partite virus. "Genome" refers to the total genetic material of the virus. "RNA genome" states that as present in virions (virus particles), the genome is in RNA form.

Some of the viruses which meet this requirement, and are therefore suitable, include Alfalfa Mosaic Virus (AlMV), ilarviruses, cucumoviruses such as Cucumber Green Mottle Mosaic virus (CGMMV), closteroviruses or tobamaviruses (tobacco mosaic virus group) such as Tobacco Mosaic virus (TMV), Tobacco Etch Virus (TEV), Cowpea Mosaic virus (CMV), and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV). Each of these groups of suitable viruses are well characterized and are well known to the skilled artisans in the field. A number of recombinant viral vectors have been used by those skilled in the art to transiently express various polypeptides in plants. See, for example, U.S. Pat. Nos. 5,316,931 and 6,042,832; and PCT International Publication, WO 00/46350, WO 96/12028 and WO 00/25574, the contents of which are incorporated herein by reference. Thus, the methods already known in the art can be used as a guidance to develop recombinant viral vectors of the present invention to deliver transacting factors.

The recombinant viral vector used in the present invention can be heterologous virus vectors. The heterologous virus vectors as referred to herein are those having a recombinant genomic component of a given class of virus (for example TMV) with a movement protein encoding nucleic acid sequence of the given class of virus but coat protein (either a full-length or truncated but functional) nucleic acid sequence of a different class of virus (for example AlMV) in place of the native coat protein nucleic acid sequence of the given class of virus. Likewise, native movement protein nucleic acid sequence instead of the coat protein sequence is replaced by heterologous (i.e. not native) movement protein from another class of virus. For example, a TMV genomic component having an AlMV coat protein is one such heterologous vector. Similarly, an AlMV genomic component having a TMV coat protein is another such heterologous vector. The vectors are designed such that these vectors, upon infection, are capable of replicating in the host cell and transiently expressing the carrier protein in the host cell.

In an aspect of the invention, both viral vectors and transgenic plants are used to express the carrier proteins of the present invention in cells of a host plant by taking advantage of a transactivation system is provided. The transactivation system has two components: (i) a transgenic plant and (ii) a recombinant viral vector. The genetically transformed cells of the host plant having integrated into their nuclear genome, an inactive or silenced carrier protein encoding nucleic acid sequence, are capable of encoding the carrier protein only upon activation of the silenced sequence. To activate the silenced sequence, a recombinant RNA viral vector is used that is capable of infecting the cells of the host plant and encoding therein a factor for activating the expression of inactive or silenced carrier protein nucleic acid sequence. The carrier protein encoding nucleic acid sequence may be silenced by placing a blocking sequence between promoter sequence and the carrier protein encoding nucleic acid sequence. The blocking sequence (e.g., a selectable marker element or any other nucleic acid sequence (stuffer) should be sufficient enough to block the promoter's ability to drive expression of the gene. The blocking sequence must be flanked on each side by a recombinase target site (e.g., "FRT" site) with a defined 5' to 3' orientation. The FRT refers to a nucleic acid sequence at which the product of the FLP gene, i.e., FLP recombinase, can catalyze the site-specific recombination. In addition to the genomic elements necessary for infection, replication, movement and spread of the viral vectors, the vectors contain sequences encoding a recombinase (e.g., FLP) or other factor (e.g., GAL4-VP16) to activate the silenced carrier protein encoding nucleic acid sequence.

In accordance with the present invention, the host plants included within the scope of the present invention are all species of higher and lower plants of the Plant Kingdom. Mature plants, seedlings, and seeds are included in the scope of the invention. A mature plant includes a plant at any stage in development beyond the seedling. A seedling is a very young, immature plant in the early stages of development. Specifically, plants that can be used as hosts to produce foreign sequences and polypeptides include and are not limited to Angiosperms, Bryophytes such as Hepaticae (liverworts) and Musci (mosses); Pteridophytes such as ferns, horsetails, and lycopods; Gymnosperms such as conifers, cycads, Ginkgo, and Gnetales; and Algae including Chlorophyceae, Phaeophpyceae, Rhodophyceae, Myxophyceae, Xanthophyceae, and Euglenophyceae.

Host plants used for the production of carrier proteins can be grown either in vivo and/or in vitro depending on the type of the selected plant and the geographic location. It is important that the selected plant is amenable to cultivation under the appropriate field conditions and/or in vitro conditions including cell culture.

Among angiosperms, the use of crop and/or crop-related members of the families are particularly contemplated. The plant members used in the present methods also include interspecific and/or intergeneric hybrids, mutagenized and/or genetically engineered plants. These families include and not limited to Leguminosae (Fabaceae) including pea, alfalfa, and soybean; Gramineae (Poaceae) including rice, corn, wheat; Solanaceae particularly of the genus *Lycopersicon*, particularly the species *esculentum* (tomato), the genus *Solanum*, particularly the species *tuberosum* (potato) and *melongena* (eggplant), the genus *Capsicum*, particularly the species *annum* (pepper), tobacco, and the like; Umbelliferae, particularly of the genera *Daucus*, particularly the species *carota* (carrot) and *Apium*, particularly the species graveolens duke, (celery) and the like; Rutaceae, particularly of the genera *Citrus* (oranges) and the like; Compositae, particularly the genus *Lactuca*, and the species *sativa* (lettuce), and the like and the Family Cruciferae, particularly of the genera *Brassica* and *Sinapis*. Examples of "vegetative" crop members of the family Brassicaceae include, but are not limited to, digenomic tetraploids such as *Brassica juncea* (L.) Czern. (mustard), *B. carinata* Braun (ethopian mustard), and monogenomic diploids such as *B. oleracea* (L.) (cole crops), *B. nigra* (L.) Koch (black mustard), *B. campestris* (L.) (turnip rape) and *Raphanus sativus* (L.) (radish). Examples of "oil-seed" crop members of the family Brassicaceae include, but are not limited to, *B. napus* (L.) (rapeseed), *B. campestris* (L.), *B. juncea* (L.) Czern. and *B. tournifortii* and *Sinapis alba* (L.) (white mustard). Flax plants are also contemplated.

Particularly preferred host plants are those that can be infected by AlMV. For example, it is known in the art that alfalfa mosaic virus has full host range. Other species that are known to be susceptible to the virus are: *Abelmoschus esculentus, Ageratum conyzoides, Amaranthus caudatus, Amaranthus retroflexus, Antirrhinum majus, Apium graveolens, Apium graveolens* var. *rapaceum, Arachis hypogaea, Astragalus glycyphyllos, Beta vulgaris, Brassica campestris* ssp. *rapa, Calendula officinalis, Capsicum annuum, Capsi-* cum frutescens, Caryopteris incana, Catharanthus roseus, Celosia argentea, Chemanthus cheiri, Chenopodium album, Chenopodium amaranticol, Chenopodium murale, Chenopodium quinoa, Cicer arietinum, Cichium endiva, Ciandrum sativum, Crotalaria spectabilis, Cucumis melo, Cucumis sativus, Cucurbita pepo, Cyamopsis tetragonoloba, Daucus carota (var. sativa), Dianthus barbatus, Dianthus caryophyllus, Emilia sagittata, Fagopyrum esculentum, Glycine max, Gomphrena globosa, Helianthus annuus, Lablab purpureus, Lactuca sativa, Lathyrus odatus, Lens culinaris, Linum usitatissimum, Lupinus albus, Lycopersicon esculentum, Macroptilium lathyroides, Malva parvifla, Matthiola incana, Medicago hispida, Medicago sativa, Melilotus albus, Nicotiana bigelovii, Nicotiana clevelandii, Nicotiana debneyi, Nicotiana glutinosa, Nicotiana megalosiphon, Nicotiana rustica, Nicotiana sylvestris, Nicotiana tabacum, Ocimum basilicum, Petuniaxhybrida, Phaseolus lunatus, Phaseolus vulgaris, Philadelphus, Physalis flidana, Physalis peruviana, Phytolacca americana, Pisum sativum, Solanum demissum, Solanum melongena, Solanum nigrum, Solanum nodiflum, Solanum rostratum, Solanum tuberosum, Sonchus oleraceus, Spinacia oleracea, Stellaria media, Tetragonia tetragonioides, Trifolium dubium, Trifolium hybridum, Trifolium incarnatum, Trifolium pratense, Trifolium repens, Trifolium subterraneum, Tropaeolum majus, Viburnum opulus, Vicia faba, Vigna radiata, Vigna unguiculata, Vigna unguiculata ssp. sesquipedalis, and Zinnia elegans.

In an aspect, the present invention also includes methods for stimulating an immune response in an animal. The use of carrier protein of the invention to stimulate immune response is described in more detail in the following Examples section. Specifically, the experiments demonstrate, for example, that the immunogenic heterologous polypeptides containing B-cell and T-cell epitopes in the carrier fusion protein stimulated pathogen specific immune responses. Surprisingly, the target specific immunogenicity of antigenic determinants fused to carrier molecule of the present invention is significantly superior to that of antigenic determinants administered alone without the carrier molecule. Further, the experiments demonstrate that it is possible to generate a humoral immune response to an internally inserted epitope-containing polypeptide segments Although the in vivo data reported herein were generated in experiments employing murine assays for the generation of antibodies against the carrier proteins, the fundamental principles are applicable to humans as well as other animals such as rabbits, pigs, goats, monkeys and chimpanzees. Given the disclosure of the subject application and the general knowledge of one skilled in the art, it is a matter of routine experimentation to select heterologous polypeptides of interest and incorporate such polypeptides of interest into a carrier molecule for use as an immunogen. One of skill in the art can identify heterologous polypeptides with B-cell epitopes which have the ability to drive a strong humoral immune response following administration to an animal. The B-cell epitope which is selected will depend upon the intended use of the carrier protein. For instance, if the carried protein is to be used as a vaccine, the heterologous polypeptides can be derived from a protein which is expressed by a virus, bacteria or other infectious organism associated with causing a disease. The heterologous polypeptide, which is selected, should be one which contains epitopes which elicit strong immune responses. In general, this will include proteins found on the surface of the infectious organism which are involved in binding and to which antibodies have a high degree of access.

The selection of immunogenic heterologous polypeptides is not limited to proteins associated with infectious organisms. For instance, the carrier protein containing an internally (or at the N or C-terminus) inserted polypeptide from a prostate-specific antigen may be used to induce a strong immune response. One of skill in the art will recognize that any heterologous polypeptide containing one or more B-cell or T-cell epitopes, which is capable of driving a humoral immune response can be included as part of the carrier protein of the present invention. Many such heterologous polypeptides are known and others can be determined through routine experimentation.

In some instances, it is desired to stimulate cytotoxic T-cells as part of a cellular immune response. In such instances, heterologous polypeptides with T-cell epitopes are fused to the carrier molecule, preferably inserted internally within the carrier. Cytotoxic T-cells play an important role in the surveillance and control of viral infections, bacterial infections, parasitic infections and cancer, for example. protocols of T-cell activation allow the triggering of more selective cytotoxic T-cell responses with greater therapeutic effectiveness.

Generally, the fusion of peptides to the C-terminus of carrier molecule with a cleavage site in between, may generate a desirable construct, which is cleavable, in vivo, by the recombinant carrier protein-specific cleavage agent. The carrier protein-specific cleavage agent (e.g., proteases) cleaves carrier protein fusion after a C-terminal residue thereby releasing the C-terminal peptide.

Thus, the carrier protein based vaccine can be used to drive a cellular and/or humoral immune response depending on the type of heterologous polypeptides fused to the carrier protein. The therapeutic amount of the carrier protein given to an animal species will be determined as that amount deemed effective in eliciting the desired immune response. The carrier protein is administered in a pharmaceutically acceptable or compatible carrier or adjuvant. Accordingly, the present invention also encompasses pharmaceutical compositions for the administration of carrier proteins. Examples of specific diseases which can be treated in this manner include, for example, infection with HIV, cancer, gastrointestinal diseases, respiratory infections etc. The pharmaceutical compositions are prepared by methods known to one of skill in the art. In general, the carrier protein is admixed with a carrier and other necessary diluents which are known in the art to aid in producing a product which is stable and administrable. Administration of the pharmaceutical composition can be accomplished by several means known to those of skill in the art. These include, i.p., oral, intradermal, subcutaneous, intranasal, intravenous or intramuscular. Typically patients to be treated are dosed subcutaneously with the carrier proteins once per week for several weeks. However, dosing can also be done orally or intranasally over a similar length of time. The result is a reduction of the allergic and/or autoimmune responses.

In addition to the conventional vaccination methods, the present invention can be used for DNA vaccination. In this method, DNA encoding the appropriate carrier protein is introduced into the cells of an organism. Within these cells, the epitope-containing carrier protein is directly expressed. Direct expression of the carrier proteins of the present invention by endogenous cells of a vaccinated animal allows for the continual stimulation of humoral and cellular immune responses over an extended period of time. Direct expression can be accomplished by introducing DNA constructs which encode the desired carrier protein into the cells of an animal. The constructs typically contain promoter elements and other transcriptional control elements which direct the expression of the carrier protein. Introduction of the DNA construct can be by any conventional means including direct injection. The preferred administration site is muscle tissue. This direct expression is in contrast to standard immunization protocols whereby the vaccine is injected at a single site one or more times. Following injection, the vaccine is disseminated to lymphoid organs where a single immune response occurs.

EXAMPLES

The examples presented below are provided as a further guide to one of ordinary skill in the art, and are not to be construed as limiting the invention in any way.

Example 1

Construction of Carrier Molecules and Carrier Proteins

This example addresses construction of the carrier protein expression vector for expression in prokaryotic and eukaryotic cells.

Figure 1:
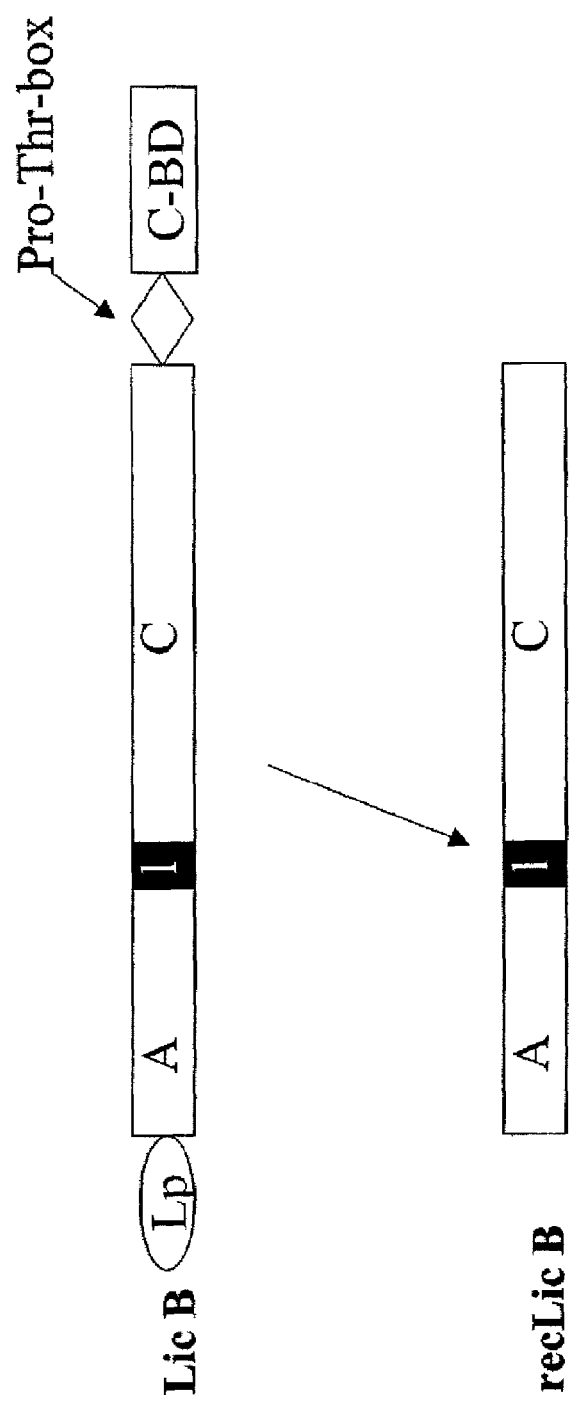
FIG. 1. A: Schematic representation of engineering of recombinant LicKM carrier molecule. 1 is the loop structure. A indicates the region upstream of the loop structure. C indicates the region downstream of the loop structure. To create LicKM, the gene encoding Lic B was split at the loop region and assembled as shown. Unique cloning sites were created during engineering. The nucleic acid sequence for engineered 30 molecule LicKM (SEQ ID NO: 1) is shown in part B of the figure. The split was done by PCR using specific primers. PCR resulted in 2 sub clones (FIG. 1A) designated as A (159 nucleotides, 364 through 522) and C (486 nucleotides, 523 through 1009). In final clone fragment A was cloned downstream of fragment C preserving the original amino acid composition.

Shown in FIG. 1 is a schematic representation of engineering of recombinant carrier molecules LicKM and recLicB. Letter "l" indicates the loop structure, A indicates the region (domain) upstream of the loop structure and C indicates the region (domain) downstream of the loop structure. To create LicKM the gene encoding a mature Lic B was split at the loop region and assembled as shown. Unique cloning sites were created during engineering. The sequence for the engineered gene (LicKM) is shown in part B of FIG. 1.

The LicKM was created in 2 step PCR cloning. 5 and 3' primers were used to amplify the lic B gene into 2 fragments designated as A (159 nucleotides of the lic B gene, 365 through 522) and C (486 nucleotides of the lic B gene, 523 through 1009). In the final clone, fragment A was cloned downstream of fragment C preserving the original amino acid composition.

The following are the specific primers used

```
Fragment C:
5' primer:
                                    (SEQ ID NO: 10)
5' gga tcc ATG GGC GGT TCA TAT CCG TAT-3'

3' primer:
                                    (SEQ ID NO: 11)
5' g cag aga TCT ATA TTC CCT GTC AAG GGT-3'

Fragment A:
5' primer:
                                    (SEQ ID NO: 12)
5' aga tcc ATG GTG GTA AAT ACG CCT TTT-3'

3' primer:
                                    (SEQ ID NO: 13)
5' g cac aga TCT ACC GTT AGG ATA GTA TTT TAC-3'.
```

Shown in FIG. 1C is a schematic of construction of rec LicB from the wildtype LicB.

Example 2

Cloning and Expression of GFP Using recLic B

Figure 2:
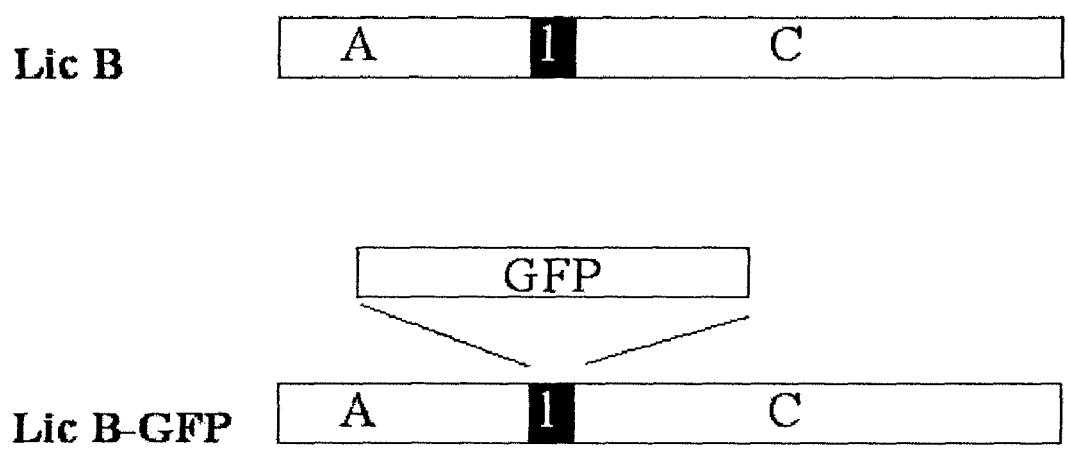
FIG. 2. Schematic representation of cloning of GFP into the loop structure of rec Lic B to obtain recombinant Lic B-GFP. The coding region of GFP was PCR amplified and cloned into the open reading frame of LicB.

The recLic B was symbolically divided into 3 regions as shown in the FIG. 2; l is the loop structure. The region (domain) upstream of the loop structure is indicated as A and downstream of loop structure is indicated as C. To use the recLic B as a carrier molecule unique cloning sites (BamHI and BglI) were introduced into the loop region of the gene. The gene encoding GFP (green fluorescent protein) was cloned into the loop region of recLic B to obtain recLic B-GFP (FIG. 2). The recombinant protein was expressed using both *Esherichia coli* and yeast expression system (FIG. 3). Target polypeptides can be inserted not only into the loop structure as it is shown in this example but can also be fused to the N or C terminus of carrier protein.

Example 3

Fermentation and Carrier Protein Recovery

*E. coli* dH5alpha cells transformed with recLic B-GFP constructs were cultured or fermented by overnight culturing process in LB media. The fermentation was continued for 12 h and harvested at a cell density of $10^4$. Two liters of cell culture or fermentation broth were divided into 1 liter containers//bottles and centrifuged at 10,000 rpm for 30 min in a centrifuge. The supernatant was discarded and the pellet was used to recover the carrier protein.

Example 4

Cloning and Expression of Various Target Polypeptides Using the Engineered LicKM This example addresses the cloning and expression of the following three target polypeptides using the engineered LicKM:
a. Peptide from G protein of respiratory syncytial virus (24 a.a.)
b. GFP (27 kD)
c. IFNα. (19 kD)

To demonstrate the capacity of engineered LicKM as a carrier molecule, 3 constructs were created where the target sequences polypeptides (a) fragment of DNA encoding 24 amino acid peptide from respiratory syncytial virus G protein, (b) open reading frame of GFP or (c) open reading frame of human interferon α were PCR amplified and cloned into the open reading frame of engineered LicKM as shown in FIG. 4. These three engineered target polypeptides were expressed in *E. coli* as shown in FIG. 5 and yeast (data not shown). Shown in FIG. 5A is a zymogram of lichenase activity in bacterial extracts detected in the presence of 0.1% lichenan as substrate. Proteins were separated in 12% PAGE. The gel was loaded with proteins extracted from *E. coli* strain XL-1 blue. C is a negative control. LicKM is engineered carrier molecule. LicKM-RSV, LicKM-GFP, and LicKM-IFNα are engineered proteins containing respective target polypeptide. FIG. 5B shows the results of Western blot analysis. Proteins were separated in 12% PAGE, electroblotted onto nylon membrane and reacted with monoclonal antibodies specific for peptide from RSV G protein. Antibodies reacted with LicKM-RSV, RSV positive control (RSV (C+)) and plant virus coat protein containing identical peptide (RSV (plant)). Extracts from LicKM that did not contain target peptide had no specificity to RSV antibodies.

Example 5

Immunization of Mice with LicKM-RSV Containing 24 Amino acid Peptide from RSV G Protein Eight-week-old female balB/c mice were immunized with 200 μg per dose of recombinant LicKM-RSV engineered to express the 24 amino acid (171-191 of G protein) of RSV G protein (Johnson et al., 2004, J Virol. 2004 June; 78(11):

6024-32). Three immunizations of 0.1 ml were administered intra-peritoneally at intervals of 2 weeks (first dose with complete Freund's adjuvant (CFA) at a 1:1, vol:vol ratio, second dose with incomplete Freund's adjuvant (CFA) at a 1:1, vol:vol ratio and third dose without any adjuvant). An equal quantity of LicKM was used as a control. Samples of pre-immune sera were collected 1 day before first dose of antigen. Twelve (12) days after each immunization serum samples were obtained from individual mice and RSV-specific antibody titers assessed. Antigen-specific antibody analysis of serum was performed using a solid phase enzyme-linked immunoabsorbant assay (ELISA). ELISA plates (Nunc Polysorp, Denmark) were coated with 100 µl per well (1.0 µg per well) of Recombinant AlMV containing identical peptide from RSV G protein (10 µg/ml in Phosphate-buffered saline) overnight at room temperature (RT; about 25° C.). Coated plates were washed 3× with PBS-Tween (0.05%) and then blocked with 0.5% of I-block (Tropix) in PBS-Tween at RT for at least 1 hour. A series of dilutions of sera were added to the plates (30 µl/well) for 2 to 4 hours at RT. The plates were then washed 3× with PBS-Tween and peroxidase-conjugated secondary antibodies (goat anti-mouse IgG, either whole molecule or gamma chain specific), were added (100 µl per well) at a final dilution of 1:10,000 in PBS-Tween, for 1 hour at RT. Plates were then washed 5× with PBS-Tween and OPD (Sigma Fast™) substrate added (100 µl/well) in phosphate-citrate buffer containing urea, for 30 min at RT in the dark. The reaction was stopped with 2M $H_2SO_4$ (50 µl per well) and the color change resulting from bound specific antibody measured at 490 nM in an ELISA plate-reader (Spectramax Plus[384]). The results, expressed in O.D. units, are shown in FIG. 6.

Example 6

Engineering and Experimental Immunization of Mice with LicKM-F200 Containing 200 Amino Acid Portion of RSV F Protein Engineering of LicKM-F200 was carried out as follows: As template DNA, plasmid DNA containing cDNAs for F, G, and M genes of RSV obtained from National Institute of Health, USA, was used (Johnson et al., 2004, J Virol. 2004 June; 78(11):6024-32).

For cloning a portion of F gene encoding amino acids 324 to 524 was amplified using 5'-GCAC AGATCT GGGTC-CAACATCTGTTTAAC-3' (SEQ ID NO:14). and 5'-GCAC AAGCTT ATTTGTGGTGGATTTACCA-3'(SEQ ID NO:15). as 5' and 3' primers. PCR amplified fragment was digested and cloned into final vector using unique restriction sites introduced during PCR reaction (BglII site at 5'- and HindIII at 3'-end, respectively). Target DNA was cloned into E. coli, agrobacterial and plant virus expression vectors. Results described in this example obtained using LicKM-F200 where target gene is cloned and expressed plant virus vector D4.

For expression, plants were inoculated with in vitro synthesized transcripts of LicKM-F200. Plant inoculations were carried out using the prior art known procedures. See, PCT International Publication, WO 00/46350 for guidance on infectious RNA transcripts and procedures for viral infection. Two weeks after inoculation samples were collected for analysis of target protein expression as well as recovery. Recombinant protein maintained enzymatic activity (FIG. 7A) and was recognized by antibodies specific to LicKM (FIG. 7B).

For stimulating immune response, eight-week-old female balB/c mice were immunized with 200 µg per dose of recombinant LicKM-F200 engineered to express the 200 amino acids (amino acid 324 to 524 of F protein) of RSV F protein. Three doses of antigen (0.1 ml/dose) were administered intra-peritoneally at intervals of 2 weeks (first dose with complete Freund's adjuvant (CFA) at a 1:1, vol:vol ratio, second dose with incomplete Freund's adjuvant (CFA) at a 1:1, vol:vol ratio and third dose without any adjuvant). An equal quantity of LicKM was used as a control. Samples of pre-immune sera were collected 1 day before first dose of antigen. Twelve (12) days after each immunization serum samples were obtained from individual mice and RSV-specific antibody titers assessed. Antigen-specific antibody analysis of serum was performed using a solid phase enzyme-linked immunoabsorbant assay (ELISA). ELISA plates (Nunc Polysorp, Denmark) were coated with 100 µl per well (1.0 µg per well) of inactivated RSV Long strain (Hy Test, 10 µg/ml in Phosphate-buffered saline) overnight at room temperature (RT; about 25° C.). Coated plates were washed 3× with PBS-Tween (0.05%) and then blocked with 0.5% of I-block (Tropix) in PBS-Tween at RT for at least 1 hour. A series of dilutions of sera were added to the plates (30 µl/well) for 2 to 4 hours at RT. The plates were then washed 3× with PBS-Tween and peroxidase-conjugated secondary antibodies (goat anti-mouse IgG, either whole molecule or gamma chain specific), were added (100 µl per well) at a final dilution of 1:10,000 in PBS-Tween, for 1 hour at RT. Plates were then washed 5× with PBS-Tween and OPD (Sigma Fast™) substrate added (100 µl/well) in phosphate-citrate buffer containing urea, for 30 min at RT in the dark. The reaction was stopped with 2M $H_2SO_4$ (50 µl per well) and the color change resulting from bound specific antibody measured at 490 nM in an ELISA plate-reader (Spectramax Plus[384]). The results, expressed in O.D. units, are shown in FIG. 8.

Example 7

Engineering and Experimental Immunization of Mice with LicKM-PAD4 Containing 145 Amino Acid Domain Four of Anthrax PA Protein Engineering of LicKM-PAD4 was carried out as follows: As template DNA, E. coli plasmid DNA containing whole Domain four (amino acids 621 to 760) of anthrax protective antigen was obtained from NMRC (Moayeri et al., 2004, Curr Opin Microbiol., 7(1):19-24).

For cloning Domain four encoding amino acids 621 to 760 was amplified using 5' GCACAGATCTAATATTTTAATAA-GAGATAAACG 3' (SEQ ID NO:16). and 5'GCACAAGCTT TCCTATCTCATAGCCTTTTT 3' (SEQ ID NO:17). as 5' and 3' primers. PCR amplified fragment was digested and cloned into final vector using unique restriction sites introduced during PCR reaction (BglII site at 5'- and HindIII at 3'-end, respectively). Target DNA was cloned into E. coli, agrobacterial and plant virus expression vectors. Results described in this example obtained using LicKM-PAD4 where target gene is cloned and expressed plant virus vector D4.

For expression, tobacco plants were inoculated with in vitro synthesized transcripts of LicKM-PAD4. Plant inoculations procedures remain the same as in the above example. Two weeks after inoculation tissue samples were collected for analysis of target protein expression as well as recovery. Recombinant protein was recognized by antibodies specific to protective antigen of anthrax (FIG. 9).

For inducing immune response, eight-week-old female balB/c mice were immunized with 200 µg per dose of recombinant LicKM-PAD4 engineered to express the 145 amino acid (amino acids 621 to 760 of PA protein) of anthrax PA protein. Three immunizations of 0.1 ml were administered intra-peritoneally at intervals of 2 weeks (first dose with complete Freund's adjuvant (CFA) at a 1:1, vol:vol ratio, second dose with incomplete Freund's adjuvant (CFA) at a 1:1, vol:vol ratio and third dose without any adjuvant). An equal quantity of LicKM was used as a control. Samples of pre-immune sera were collected 1 day before first dose of antigen. Twelve (12) days after each immunization serum samples were obtained from individual mice and RSV-specific antibody titers assessed. Antigen-specific antibody analysis of serum was performed using a solid phase enzyme-linked immunoabsorbant assay (ELISA). ELISA plates (Nunc Polysorp, Denmark) were coated with 100 µl per well (1.0 µg per well) of recombinant PA (10 µg/ml in Phosphate-buffered saline) overnight at room temperature (RT; about 25° C.). Coated plates were washed 3× with PBS-Tween (0.05%) and then blocked with 0.5% of I-block (Tropix) in PBS-Tween at RT for at least 1 hour. A series of dilutions of sera were added to the plates (30 µl/well) for 2 to 4 hours at RT. The plates were then washed 3× with PBS-Tween and peroxidase-conjugated secondary antibodies (goat anti-mouse IgG, either whole molecule or gamma chain specific), were added (100 µl per well) at a final dilution of 1:10,000 in PBS-Tween, for 1 hour at RT. Plates were then washed 5× with PBS-Tween and OPD (Sigma Fast™) substrate added (100 µl/well) in phosphate-citrate buffer containing urea, for 30 min at RT in the dark. The reaction was stopped with 2M $H_2SO_4$ (50 µl per well) and the color change resulting from bound specific antibody measured at 490 nM in an ELISA plate-reader (Spectramax Plus[384]). The results, expressed in O.D. units, are shown in FIG. 10.

LicKM-HbsAg was also expressed in plants. Tobacco plants are used to produce target antigens as fusions with carrier protein.

All publications, patents and patent applications mentioned in the specification are indicative of the level of those skilled in the art to which this invention pertains. All publications, patents and patent applications referred to herein are incorporated herein by reference to the same extent as if each individual publication or patent application was specifically and individually indicated to be incorporated by reference. While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

The invention claimed is:

1. A recombinant polypeptide comprising a modified lichenase B polypeptide that has an amino acid sequence with at least 90% sequence identity to amino acids 14-231 of SEQ ID NO: 3, or an amino acid sequence with at least 90% sequence identity to amino acids 8-226 of SEQ ID NO: 6, wherein the modified lichenase B polypeptide is optionally fused to a heterologous polypeptide sequence that is not found in the modified lichenase B polypeptide.

2. The recombinant polypeptide of claim 1, wherein the modified lichenase B polypeptide is encoded by SEQ ID NO: 1 or 5.

3. The recombinant polypeptide of claim 1, wherein the modified lichenase B polypeptide comprises the sequence set forth in SEQ ID NO: 3 or SEQ ID NO: 6.

4. The recombinant polypeptide of claim 1, wherein the heterologous polypeptide sequence is fused to the modified lichenase B polypeptide so as to create a fusion protein.

5. The recombinant polypeptide of claim 1, wherein the modified lichenase B polypeptide has an amino acid sequence with at least 95% sequence identity to amino acids 14-231 of SEQ ID NO: 3, or at least 95% sequence identity to amino acids 8-226 of SEQ ID NO: 6.

6. The recombinant polypeptide of claim 1, wherein the modified lichenase B polypeptide has the sequence of amino acids 14-231 of SEQ ID NO: 3, or the amino acid sequence of amino acids 8-226 of SEQ ID NO: 6.

7. The recombinant polypeptide of claim 4, wherein the modified lichenase B polypeptide is fused to two or more heterologous epitope-containing polypeptide segments so as to create a fusion protein.

8. The recombinant polypeptide of claim 4, wherein the heterologous polypeptide is fused to the N-terminus or C-terminus of the modified lichenase B polypeptide, or is fused internally into the modified lichenase B polypeptide.

9. A method comprising administering to an animal a composition comprising the recombinant polypeptide of claim 1, wherein the recombinant polypeptide comprises:
   (a) a modified lichenase B polypeptide that has an amino acid sequence with at least 90% sequence identity to amino acids 14-231 of SEQ ID NO: 3, or an amino acid sequence with at least 90% sequence identity to amino acids 8-226 of SEQ ID NO: 6, fused to
   (b) a heterologous polypeptide sequence that is not found in the lichenase B polypeptide, wherein the heterologous polypeptide comprises at least one disease-associated antigen, wherein the composition further comprises a pharmaceutically acceptable carrier medium or adjuvant, and wherein the administering stimulates an immune response to the at least one disease-associated antigen in the animal.

10. The method of claim 9, wherein the recombinant polypeptide has lichenase activity.

11. The method of claim 9, wherein the modified lichenase B polypeptide has an amino acid sequence with at least 95% sequence identity to amino acids 14-231 of SEQ ID NO: 3, or an amino acid sequence with at least 95% sequence identity to amino acids 8-226 of SEQ ID NO: 6.

12. The method of claim 9, wherein the heterologous polypeptide is fused to the N-terminus or C-terminus of the modified lichenase B polypeptide, or is fused internally into the modified lichenase B polypeptide.

13. The recombinant polypeptide of claim 1, wherein the heterologous polypeptide sequence comprises a growth factor, cytokine, ligand, receptor, inhibitor, antigen, epitope, T cell epitope, B cell epitope, antibody, hydrolase, green fluorescent protein, interferon, interleukin, pathogen-associated protein, or toxin.

14. The recombinant polypeptide of claim 1, wherein the heterologous polypeptide sequence comprises a vaccine antigen.

15. The recombinant polypeptide of claim 1, further comprising a tag usable for separation or purification, or both.

16. The recombinant polypeptide of claim 15, wherein the tag is His 6.

17. The recombinant polypeptide of claim 16, further comprising an enzymatic cleavage site.

18. The recombinant polypeptide of claim 17, wherein the cleavage site is located between the heterologous polypeptide and the modified lichenase B polypeptide.

19. The recombinant polypeptide of claim 1, further comprising a tag and a cleavage site, wherein the cleavage site is located adjacent to the tag.

20. The recombinant polypeptide of claim 1, further comprising a linker.

* * * * *

UNITED STATES PATENT AND TRADEMARK OFFICE
CERTIFICATE OF CORRECTION

PATENT NO. : 8,173,408 B2
APPLICATION NO. : 12/625129
DATED : May 8, 2012
INVENTOR(S) : Vidadi Yusibov, Vadim Mett and Konstantin Musiychuk It is certified that error appears in the above-identified patent and that said Letters Patent is hereby corrected as shown below:

Page 1, column 2 (OTHER PUBLICATIONS), lines 1 and 2, delete "Sen et......23*"
and insert same on Page 1, column 2, line 2 as a separate entry.

Col. 32, line 4, delete "His 6" and insert --His6--, therefor.

Signed and Sealed this
Fourteenth Day of August, 2012

David J. Kappos
*Director of the United States Patent and Trademark Office*

SEQUENCE LISTING

```
<160> NUMBER OF SEQ ID NOS: 17

<210> SEQ ID NO 1
<211> LENGTH: 710
<212> TYPE: DNA
<213> ORGANISM: Artificial Sequence
<220> FEATURE:
<223> OTHER INFORMATION: Primer

<400> SEQUENCE: 1
ggaattcagg aatgagagga tcgcatcacc atcaccatca cggatccatg ggcggttcat      60
atccgtataa aagcggtgaa tatcgtacaa aatcattttt cggatacggt tattatgaag     120
taagaatgaa agctgccaaa aacgtaggaa ttgtttcatc tttcttcact tatacaggac     180
cttcggacaa caatccatgg gacgaaatcg atatcgagtt tttaggaaag gacacaacta     240
aagttcagtt caactggtac aaaaatggag tcggtggaaa cgagtatttg cacaatcttg     300
gattcgatgc ttcccaggat tttcatacat atggatttga atggaggccg gattatatag     360
acttctatgt tgacggcaaa aaagtttatc gtggaaccag gaacatacct gttactcccg     420
gcaaaattat gatgaatttg tggccaggaa taggagtgga tgaatggttg ggacgttacg     480
acggaagaac tcctttgcag gcggagtacg aatatgtaaa atactatcct aacggtagat     540
ccatggtggt aaatacgcct tttgttgcag tgttttcgaa ctttgactcc agtcagtggg     600
aaaaagcgga ttgggcgaac ggttcggtgt tcaactgtgt ttggaagcct tcacaggtga     660
cattttcgaa cggtaaaatg attttgaccc ttgacaggga atatagatct                710

<210> SEQ ID NO 2
<211> LENGTH: 778
<212> TYPE: DNA
<213> ORGANISM: Artificial Sequence
<220> FEATURE:
<223> OTHER INFORMATION: Primer

<400> SEQUENCE: 2
```

```
atgagaggat cgcatcacca tcaccatcac ggatccgcat gcgagctcgg taccccgggt    60
cgagggccca tggtaaatac gccttttgtt gcagtgtttt cgaactttga ctccagtcag   120
tgggaaaaag cggattgggc gaacggttcg gtgttcaact gtgtttggaa gccttcacag   180
gtgacatttt cgaacggtaa aatgattttg acccttgaca gggaatatgg cggttcatat   240
ccgtataaaa gcggtgaata tcgtacaaaa tcattttcg gatacggtta ttatgaagta   300
agaatgaaag ctgccaaaaa cgtaggaatt gtttcatctt tcttcactta tacaggacct   360
tcggacaaca atccatggga cgaaatcgat atcgagtttt taggaaagga cacaactaaa   420
gttcagttca actggtacaa aaatggagtc ggtggaaacg agtatttgca caatcttgga   480
ttcgatgctt cccaggattt tcatacatat ggatttgaat ggaggccgga ttatatagac   540
ttctatgttg acggcaaaaa agtttatcgt ggaaccagga catacctgt tactcccggc   600
aaaattatga tgaatttgtg gccaggaata ggagtggatg aatggttggg acgttacgac   660
ggaagaactc ctttgcaggc ggagtacgaa tatgtaaaat actatcctaa cggtgttccg   720
caagataatc ctactcctac tcctacgatt gctccttcta ctccgagatc tatctaga    778
```

<210> SEQ ID NO 3
<211> LENGTH: 234
<212> TYPE: PRT
<213> ORGANISM: Artificial Sequence
<220> FEATURE:
<223> OTHER INFORMATION: Primer

<400> SEQUENCE: 3

```
Met Arg Gly Ser His His His His His His Gly Ser Met Gly Gly Ser
  1               5                  10                  15

Tyr Pro Tyr Lys Ser Gly Glu Tyr Arg Thr Lys Ser Phe Phe Gly Tyr
                 20                  25                  30

Gly Tyr Tyr Glu Val Arg Met Lys Ala Ala Lys Asn Val Gly Ile Val
             35                  40                  45

Ser Ser Phe Phe Thr Tyr Thr Gly Pro Ser Asp Asn Asn Pro Trp Asp
         50                  55                  60

Glu Ile Asp Ile Glu Phe Leu Gly Lys Asp Thr Thr Lys Val Gln Phe
 65                  70                  75                  80

Asn Trp Tyr Lys Asn Gly Val Gly Gly Asn Glu Tyr Leu His Asn Leu
                 85                  90                  95

Gly Phe Asp Ala Ser Gln Asp Phe His Thr Tyr Gly Phe Glu Trp Arg
            100                 105                 110

Pro Asp Tyr Ile Asp Phe Tyr Val Asp Gly Lys Lys Val Tyr Arg Gly
            115                 120                 125

Thr Arg Asn Ile Pro Val Thr Pro Gly Lys Ile Met Met Asn Leu Trp
        130                 135                 140

Pro Gly Ile Gly Val Asp Glu Trp Leu Gly Arg Tyr Asp Gly Arg Thr
145                 150                 155                 160

Pro Leu Gln Ala Glu Tyr Glu Tyr Val Lys Tyr Tyr Pro Asn Gly Arg
                165                 170                 175

Ser Met Val Val Asn Thr Pro Phe Val Ala Val Phe Ser Asn Phe Asp
            180                 185                 190

Ser Ser Gln Trp Glu Lys Ala Asp Trp Ala Asn Gly Ser Val Phe Asn
        195                 200                 205

Cys Val Trp Lys Pro Ser Gln Val Thr Phe Ser Asn Gly Lys Met Ile
    210                 215                 220

Leu Thr Leu Asp Arg Glu Tyr Arg Ser Ile
                225                 230
```

<210> SEQ ID NO 4
<211> LENGTH: 258
<212> TYPE: PRT
<213> ORGANISM: Artificial Sequence
<220> FEATURE:
<223> OTHER INFORMATION: Primer

<400> SEQUENCE: 4

Met Arg Gly Ser His His His His His His Gly Ser Ala Cys Glu Leu
 1               5                  10                  15

Gly Thr Pro Gly Arg Gly Pro Met Val Asn Thr Pro Val Ala Val
                20                  25                  30

Phe Ser Asn Phe Asp Ser Ser Gln Trp Glu Lys Ala Asp Trp Ala Asn
             35                  40                  45

Gly Ser Val Phe Asn Cys Val Trp Lys Pro Ser Gln Val Thr Phe Ser
         50                  55                  60

Asn Gly Lys Met Ile Leu Thr Leu Asp Arg Glu Tyr Gly Gly Ser Tyr
 65                  70                  75                  80

Pro Tyr Lys Ser Gly Glu Tyr Arg Thr Lys Ser Phe Phe Gly Tyr Gly
                 85                  90                  95

Tyr Tyr Glu Val Arg Met Lys Ala Ala Lys Asn Val Gly Ile Val Ser
            100                 105                 110

Ser Phe Phe Thr Tyr Thr Gly Pro Ser Asp Asn Asn Pro Trp Asp Glu
        115                 120                 125

Ile Asp Ile Glu Phe Leu Gly Lys Asp Thr Thr Lys Val Gln Phe Asn
130                 135                 140

Trp Tyr Lys Asn Gly Val Gly Gly Asn Glu Tyr Leu His Asn Leu Gly
145                 150                 155                 160

Phe Asp Ala Ser Gln Asp Phe His Thr Tyr Gly Phe Glu Trp Arg Pro
                165                 170                 175

Asp Tyr Ile Asp Phe Tyr Val Asp Gly Lys Lys Val Tyr Arg Gly Thr
            180                 185                 190

Arg Asn Ile Pro Val Thr Pro Gly Lys Ile Met Met Asn Leu Trp Pro
        195                 200                 205

Gly Ile Gly Val Asp Glu Trp Leu Gly Arg Tyr Asp Gly Arg Thr Pro
    210                 215                 220

Leu Gln Ala Glu Tyr Glu Tyr Val Lys Tyr Tyr Pro Asn Gly Val Pro
225                 230                 235                 240

Gln Asp Asn Pro Thr Pro Thr Pro Thr Ile Ala Pro Ser Thr Pro Arg
                245                 250                 255

Ser Ile

<210> SEQ ID NO 5
<211> LENGTH: 711
<212> TYPE: DNA
<213> ORGANISM: Artificial Sequence
<220> FEATURE:
<223> OTHER INFORMATION: Primer

<400> SEQUENCE: 5
ggatccttaa ttaaaatgca ccatcaccat caccatggcg gttcatatcc gtataaagc      60 ggtgaatatc gtacaaaatc attttttcgga tacggttatt atgaagtaag aatgaaagct    120
gccaaaaacg taggaattgt ttcatctttc ttcacttata caggaccttc ggacaacaat    180
ccatgggacg aaatcgatat cgagtttta ggaaaggaca caactaaagt tcagttcaac     240

```
tggtacaaaa atggagtcgg tggaaacgag tatttgcaca atcttggatt cgatgcttcc      300
caggattttc atacatatgg atttgaatgg aggccggatt atatagactt ctatgttgac      360
ggcaaaaaag tttatcgtgg aaccaggaac atacctgtta ctcccggcaa aattatgatg      420
aatttgtggc aggaatagg agtggatgaa tggttgggac gttacgacgg aagaactcct       480
```
*(note: line 420→480 as printed)*

```
ttgcaggcgg agtacgaata tgtaaaatac tatcctaacg gtagatctga attcaagctt      540
gtggtaaata cgccttttgt tgcagtgttt tcgaactttg actccagtca gtgggaaaaa      600
gcggattggg cgaacggttc ggtgttcaac tgtgtttgga agccttcaca ggtgacattt      660
tcgaacggta aaatgatttt gacccttgac aggaatatt gactcgagct c              711
```

<210> SEQ ID NO 6
<211> LENGTH: 228
<212> TYPE: PRT
<213> ORGANISM: Artificial Sequence
<220> FEATURE:
<223> OTHER INFORMATION: Primer

<400> SEQUENCE: 6

```
Met His His His His His Gly Gly Ser Tyr Pro Tyr Lys Ser Gly
 1               5                  10                  15

Glu Tyr Arg Thr Lys Ser Phe Phe Gly Tyr Gly Tyr Glu Val Arg
             20                  25                  30

Met Lys Ala Ala Lys Asn Val Gly Ile Val Ser Phe Phe Thr Tyr
             35                  40                  45

Thr Gly Pro Ser Asp Asn Pro Trp Asp Glu Ile Asp Ile Glu Phe
         50                  55                  60

Leu Gly Lys Asp Thr Thr Lys Val Gln Phe Asn Trp Tyr Lys Asn Gly
 65                  70                  75                  80

Val Gly Gly Asn Glu Tyr Leu His Asn Leu Gly Phe Asp Ala Ser Gln
                 85                  90                  95

Asp Phe His Thr Tyr Gly Phe Glu Trp Arg Pro Asp Tyr Ile Asp Phe
            100                 105                 110

Tyr Val Asp Gly Lys Lys Val Tyr Arg Gly Thr Arg Asn Ile Pro Val
        115                 120                 125

Thr Pro Gly Lys Ile Met Met Asn Leu Trp Pro Gly Ile Gly Val Asp
    130                 135                 140

Glu Trp Leu Gly Arg Tyr Asp Gly Arg Thr Pro Leu Gln Ala Glu Tyr
145                 150                 155                 160

Glu Tyr Val Lys Tyr Tyr Pro Asn Gly Arg Ser Glu Phe Lys Leu Val
                165                 170                 175

Val Asn Thr Pro Phe Val Ala Val Phe Ser Asn Phe Asp Ser Ser Gln
            180                 185                 190

Trp Glu Lys Ala Asp Trp Ala Asn Gly Ser Val Phe Asn Cys Val Trp
        195                 200                 205

Lys Pro Ser Gln Val Thr Phe Ser Asn Gly Lys Met Ile Leu Thr Leu
    210                 215                 220

Asp Arg Glu Tyr
225
```

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
gcagggatcc atggtgagca agggcgag                                             28

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
gcagagatct cttgtacagc tcgtccat                                             28

<210> SEQ ID NO 9
<211> LENGTH: 6
<212> TYPE: PRT
<213> ORGANISM: Artificial Sequence
<220> FEATURE:
<223> OTHER INFORMATION: Primer

<400> SEQUENCE: 9

His His His His His His
 1               5

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
ggatccatgg gcggttcata tccgtat                                              27

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gcagagatct atattccctg tcaagggt                                             28

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
agatccatgg tggtaaatac gcctttt                                              27

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
gcacagatct accgttagga tagtatttta c                                         31

<210> SEQ ID NO 14
<211> LENGTH: 30
<212> TYPE: DNA

```
<213> ORGANISM: Artificial Sequence
<220> FEATURE:
<223> OTHER INFORMATION: Primer

<400> SEQUENCE: 14
gcacagatct gggtccaaca tctgtttaac                                          30

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
gcacaagctt atttgtggtg gatttacca                                           29

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
gcacagatct aatattttaa taagagataa acg                                      33

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
gcacaagctt tcctatctca tagccttttt                                          30
```